(12) United States Patent
Kline et al.

(10) Patent No.: US 10,137,674 B2
(45) Date of Patent: Nov. 27, 2018

(54) ELASTOMERIC LAMINATE WITH ACTIVATION THICKNESS

(71) Applicant: The Procter & Gamble Company, Cincinnati, OH (US)

(72) Inventors: Mark James Kline, Okeana, OH (US); Matthias Konrad Hippe, Sulzbach (DE); Tina Liebe, Schwalbach (DE); Jill Marlene Orr, Liberty Township, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 157 days.

(21) Appl. No.: 15/131,275

(22) Filed: Apr. 18, 2016

(65) Prior Publication Data

US 2017/0297316 A1  Oct. 19, 2017

(51) Int. Cl.
| | | |
|---|---|---|
| B32B 37/12 | (2006.01) | |
| B32B 38/00 | (2006.01) | |
| A61F 13/15 | (2006.01) | |
| B32B 7/04 | (2006.01) | |
| B32B 37/14 | (2006.01) | |
| B32B 37/00 | (2006.01) | |
| B32B 37/04 | (2006.01) | |

(52) U.S. Cl.
CPC ........ B32B 37/12 (2013.01); A61F 13/15739 (2013.01); B32B 7/045 (2013.01); B32B 37/144 (2013.01); B32B 38/1875 (2013.01); B32B 37/0076 (2013.01); B32B 37/04 (2013.01); B32B 37/14 (2013.01); B32B 2038/0028 (2013.01); B32B 2305/20 (2013.01); B32B 2309/16 (2013.01); B32B 2555/02 (2013.01)

(58) Field of Classification Search
CPC ..... B32B 37/12; B32B 37/14; B32B 38/1875; B32B 2038/0028; B32B 2309/16; B32B 2555/02
See application file for complete search history.

(56) References Cited

U.S. PATENT DOCUMENTS

| | | |
|---|---|---|
| 3,848,594 A | 11/1974 | Buell |
| 3,860,003 A | 1/1975 | Buell |
| 4,610,678 A | 9/1986 | Weisman et al. |

(Continued)

FOREIGN PATENT DOCUMENTS

| | | |
|---|---|---|
| EP | 1342563 B1 | 6/2004 |
| EP | 1783257 | 5/2007 |

(Continued)

OTHER PUBLICATIONS

International Search Report, PCT/US2017/028032, dated Oct. 6, 2017, 13 pages.

*Primary Examiner* — George R Koch
(74) *Attorney, Agent, or Firm* — Wednesday G. Shipp; Andrew J. Hagerty

(57) ABSTRACT

A method for forming an elastomeric laminate includes the steps of providing a first coverstock material; SELF'ing the first coverstock material to create a pre-SELFed coverstock layer having a primary activation pattern comprising SELF-specific land areas; providing an elastomeric layer; and joining the elastomeric layer to the pre-SELFed layer at zero relative strain, such that the elastomeric layer and pre-SELFed coverstock layer are joined at one or more bonding sites.

20 Claims, 19 Drawing Sheets

(56) References Cited

U.S. PATENT DOCUMENTS

| | | |
|---|---|---|
| 4,662,875 A | 5/1987 | Hirotsu et al. |
| 4,699,622 A | 10/1987 | Toussant et al. |
| 4,846,815 A | 7/1989 | Scripps |
| 4,892,536 A | 1/1990 | DesMarais et al. |
| 4,894,060 A | 1/1990 | Nestegard |
| 4,946,527 A | 8/1990 | Battrell |
| 4,963,140 A | 10/1990 | Robertson et al. |
| 4,990,147 A | 2/1991 | Freeland |
| 5,037,416 A | 8/1991 | Allen et al. |
| 5,151,092 A | 9/1992 | Buell et al. |
| 5,156,793 A | 10/1992 | Buell et al. |
| 5,167,897 A | 12/1992 | Weber et al. |
| 5,221,274 A | 6/1993 | Buell et al. |
| 5,242,436 A | 9/1993 | Weil et al. |
| 5,260,345 A | 11/1993 | DesMarais et al. |
| 5,269,775 A | 12/1993 | Freeland et al. |
| 5,368,584 A | 11/1994 | Clear et al. |
| 5,387,207 A | 2/1995 | Dyer et al. |
| 5,397,316 A | 3/1995 | Lavon et al. |
| 5,499,978 A | 3/1996 | Buell et al. |
| 5,507,736 A | 4/1996 | Clear et al. |
| 5,518,801 A | 5/1996 | Chappell et al. |
| 5,554,145 A | 9/1996 | Roe et al. |
| 5,569,234 A | 10/1996 | Buell et al. |
| 5,571,096 A | 11/1996 | Dobrin et al. |
| 5,575,783 A | 11/1996 | Clear et al. |
| 5,580,411 A | 12/1996 | Nease et al. |
| 5,591,152 A | 1/1997 | Buell et al. |
| 5,607,760 A | 3/1997 | Roe |
| 5,609,587 A | 3/1997 | Roe |
| 5,625,222 A | 4/1997 | Yoneda et al. |
| 5,635,191 A | 6/1997 | Roe et al. |
| 5,643,588 A | 7/1997 | Roe et al. |
| 5,691,035 A | 11/1997 | Chappell et al. |
| 5,723,087 A | 3/1998 | Chappell et al. |
| 5,804,021 A | 9/1998 | Abuto et al. |
| D402,121 S | 12/1998 | Anderson et al. |
| 5,865,823 A | 2/1999 | Curro |
| 5,882,769 A * | 3/1999 | McCormack ........... A61F 13/51 156/160 |
| 5,891,544 A | 4/1999 | Chappell et al. |
| 5,968,029 A | 10/1999 | Chappell et al. |
| 5,993,432 A | 11/1999 | Lodge et al. |
| 6,004,306 A | 12/1999 | Robles et al. |
| 6,107,537 A | 8/2000 | Elder et al. |
| 6,132,411 A | 10/2000 | Huber et al. |
| 6,410,129 B2 | 6/2002 | Zhang et al. |
| 6,432,098 B1 | 8/2002 | Kline et al. |
| 6,677,258 B2 | 1/2004 | Carroll et al. |
| 6,863,666 B2 | 3/2005 | Minato |
| 7,008,496 B2 | 3/2006 | Morman |
| 7,351,297 B2 | 4/2008 | Middlesworth et al. |
| 7,435,243 B2 | 10/2008 | Miyamoto et al. |
| 7,806,883 B2 | 10/2010 | Fossum et al. |
| 7,819,853 B2 | 10/2010 | Desai et al. |
| 7,870,652 B2 | 1/2011 | Kline et al. |
| 8,062,279 B2 | 11/2011 | Miyamoto |
| 8,124,828 B2 | 2/2012 | Kline et al. |
| D673,746 S | 1/2013 | Pung et al. |
| 8,382,736 B2 | 2/2013 | Kline et al. |
| 8,568,382 B2 | 10/2013 | Kline et al. |
| 8,569,571 B2 | 10/2013 | Kline et al. |
| 8,598,407 B2 | 12/2013 | Roe et al. |
| 8,618,350 B2 | 12/2013 | Mansfield |
| 8,690,852 B2 | 4/2014 | Macura et al. |
| 8,741,083 B2 | 6/2014 | Wennerbaeck et al. |
| 8,795,809 B2 | 8/2014 | Mansfield |
| 8,858,523 B2 | 10/2014 | Sauer et al. |
| 8,939,957 B2 | 1/2015 | Raycheck et al. |
| 8,979,815 B2 | 3/2015 | Roe et al. |
| 8,992,499 B2 | 3/2015 | Kline et al. |
| 9,060,904 B2 | 6/2015 | Hundorf et al. |
| 9,072,634 B2 | 7/2015 | Hundorf et al. |
| 9,271,880 B2 | 3/2016 | Karlsson et al. |
| 9,301,889 B2 | 4/2016 | Miyamoto |
| 2002/0105110 A1 | 8/2002 | Dobrin et al. |
| 2004/0131820 A1 | 7/2004 | Curro et al. |
| 2005/0245162 A1 | 11/2005 | McCormack et al. |
| 2007/0142815 A1 | 6/2007 | Macura et al. |
| 2007/0287982 A1 | 12/2007 | Autran et al. |
| 2009/0191779 A1* | 7/2009 | Cree ................. A61F 13/15593 442/361 |
| 2009/0258210 A1 | 10/2009 | Autran et al. |
| 2009/0311465 A1 | 12/2009 | DeJong |
| 2010/0285286 A1* | 11/2010 | Middlesworth ..... A61F 13/4902 428/196 |
| 2012/0157957 A1 | 6/2012 | Kline et al. |
| 2012/0271265 A1 | 10/2012 | Langdon |
| 2012/0330262 A1 | 12/2012 | Lawson et al. |
| 2013/0082418 A1 | 4/2013 | Curro et al. |
| 2014/0023829 A1 | 1/2014 | Broering |
| 2014/0255658 A1 | 9/2014 | Muslet et al. |
| 2015/0088088 A1 | 3/2015 | Wade et al. |
| 2017/0000660 A1 | 1/2017 | Wade et al. |

FOREIGN PATENT DOCUMENTS

| | | |
|---|---|---|
| WO | WO 95/16746 | 6/1995 |
| WO | WO 2012/145599 | 10/2012 |
| WO | WO 2015/041928 | 3/2015 |
| WO | WO 2015/041929 | 3/2015 |
| WO | WO 2017/004309 | 1/2017 |

* cited by examiner

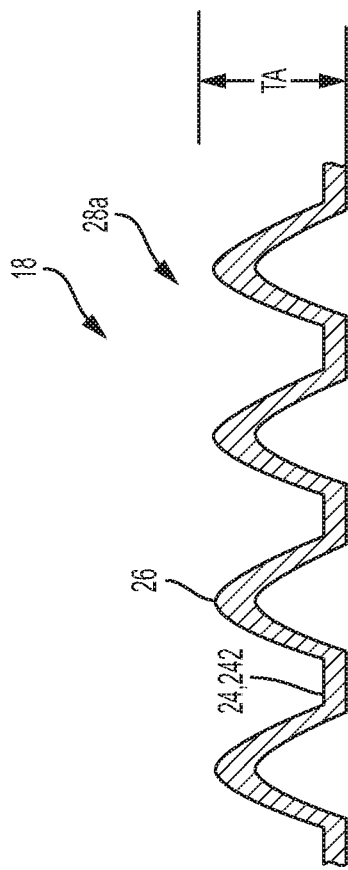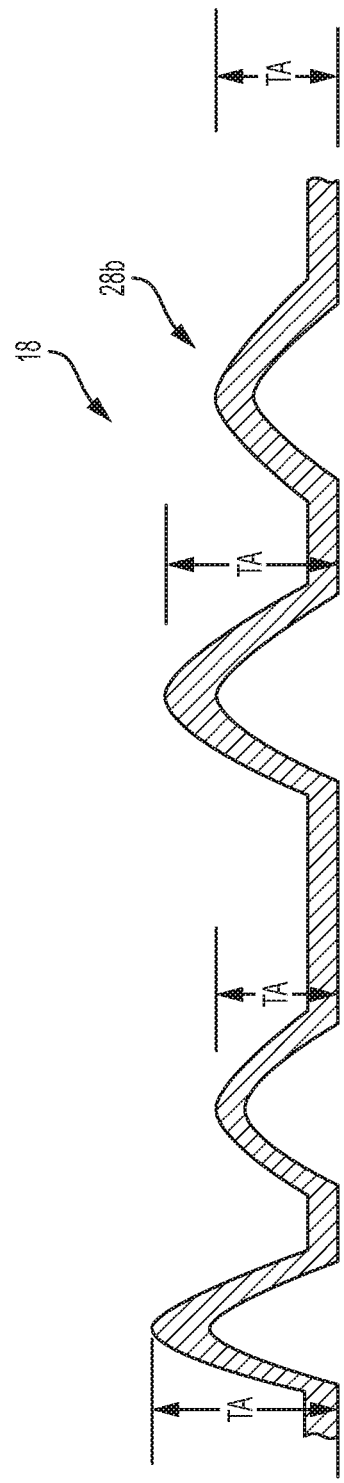

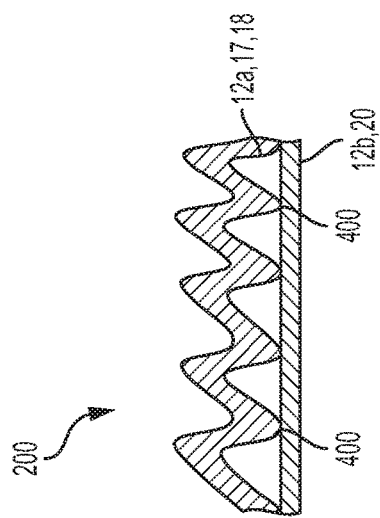
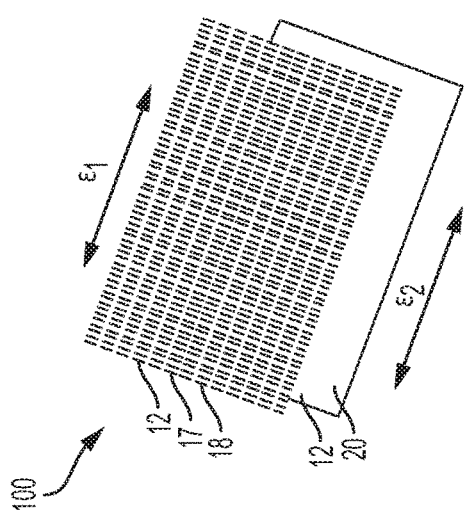
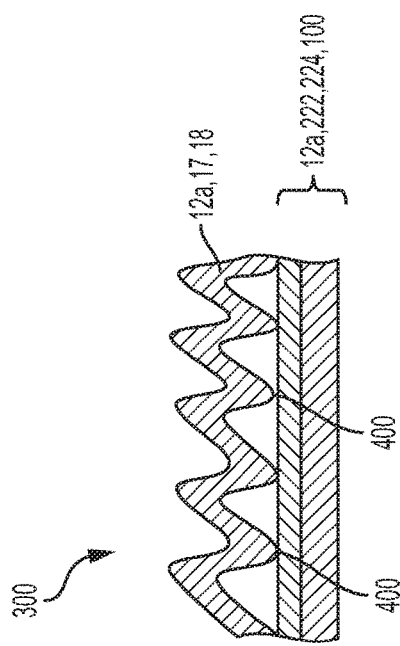

ELASTOMERIC LAMINATE WITH ACTIVATION THICKNESS

FIELD OF THE INVENTION

The present invention relates to a multi-layer elastomeric laminate and articles including the same.

BACKGROUND OF THE INVENTION

Elastomeric laminates are used in various products including absorbent articles (e.g., diapers, incontinence articles, feminine hygiene pads), clothing, body wraps, etc. Such laminates typically include an elastomeric layer that provides elasticity to the laminate and an outer layer (referred to herein as a coverstock layer) that is less stretchable but suitable for providing durability and desirable tactile properties. In this way, the laminate permits a component of an article to closely and comfortably contact the wearer while providing desirable exterior qualities.

Elastic laminates can be produced by multiple methods. For example, the laminate may be in the form a gathered laminate, wherein the coverstock layer forms rugosities when the stretchable layer is relaxed. Said gathered laminates may be formed by extending the stretchable material to a greater extent than the coverstock material at the time of lamination. Alternatively, the coverstock material may be corrugated and the elastic material may be in its relaxed state at the time of lamination. In either scenario, following lamination, the coverstock gathers or bunches and forms rugosities when the laminate is in a relaxed state.

Another type of elastomeric laminate is a zero strain laminate. During lamination, the coverstock and elastic layers are joined at approximately zero relative strain (i.e., neither layer is strained to a greater extent than the other layer). Zero strain laminates are activated by a mechanical straining process, which creates separations or deformations in the coverstock materials and renders the laminate elastically extensible.

Known elastomeric materials and laminates have limitations. Elastic materials alone may not provide desirable tactile properties and textures required for the end products in which the materials are incorporated. Further, elastic materials can be expensive and limited in the properties they can provide (e.g., limited in direction of extensibility, limited in ability to provide differential modulus, etc.). Laminates likewise may lack some desired cost efficiency and design versatility. For instance, gathered laminates can be costly to manufacture due to costs of coverstock materials that are necessary to ensure the desired amount of stretch (e.g., if the laminate is to stretch twice its relaxed length, than the coverstock should be twice as long as the elastic material). Moreover, achieving differential properties (e.g., differential modulus) can be challenging and costly as variations in the elastic material forming the stretchable layer would be necessary (e.g., different strain levels, basis weights, formulations). The manufacturing of zero strain laminates also presents challenges. The mechanical straining process may result in damage to one or more layers of the laminate. Indeed, areas of a layer that introduce a variation (e.g., a change in material and/or caliper, a bond site, or an imperfection) may result in added stress in said area, leading to weaknesses or tears in the one or more layers or in the laminate as a whole. Increasing the number of layers undergoing activation results in a greater probability that a defect in one or more locations will occur. Further, in plastically deforming the coverstock material, there is a risk that portions of the material may be completely destroyed. Weaknesses and tears can lead to exposure of the elastic material and/or excess fuzz, both of which could lead to downtime and inefficiencies in manufacturing, result in product performance issues and/or become a comfort and/or safety issue to the end user. In addition, by mechanical straining all layers at once, any defects created will extend through the entire laminate. Prevention of these problems often requires more expensive coverstock materials and/or slower process rates. Known laminates are also limited in the variations in textures, surface patterns and related properties that can be created, particularly where it is desirable to have different textures and patterns on either side of the laminate.

Therefore, there is a continued need to reduce costs and enhance efficiency in creating elastomeric laminates. There is a further need for manufacturing processes that enable differential properties in targeted regions and/or differential properties that can follow targeted pathways in a product. Likewise, it would be beneficial to provide elastomeric laminates with desirable textures on both exterior surfaces and/or that embody different activation patterns on various layers in order to more fully optimize performance.

SUMMARY OF THE INVENTION

The present invention may address one or more of these problems. In an embodiment, a method for forming an elastomeric laminate includes the steps of: providing a first coverstock material; SELF'ing the first coverstock material to create a pre-SELFed coverstock layer having a primary activation pattern comprising SELF-specific land areas; providing an elastomeric layer; and joining the elastomeric layer to the pre-SELFed layer at zero relative strain, such that the elastomeric layer and pre-SELFed coverstock layer are joined at one or more bonding sites.

In another embodiment, a method for forming an elastomeric laminate includes the steps of: providing a first coverstock material; SELF'ing the first coverstock material to create a pre-SELFed coverstock layer having a primary activation pattern comprising SELF-specific land areas; providing an elastomeric layer; elongating one of the elastomeric layer and the pre-SELFed layer to form a strained layer such that strained layer comprises a greater strain than the other of elastomeric layer and the pre-SELFed layer; and joining the elastomeric layer to the pre-SELFed layer, such that the elastomeric layer and pre-SELFed coverstock layer are joined at one or more bonding sites and form a gathered laminate.

In a further embodiment, a method for forming a hybrid gathered elastomeric laminate includes the steps of: providing a zero strain laminate; providing a second layer; elongating one of the zero stain laminate and the second layer to form a strained layer such that strained layer comprises a greater strain than a nonstrained layer, the nonstrained layer comprising the other of zero strain laminate and the second layer; and joining the zero strain laminate to the second layer, such that the zero strain laminate and second layer are joined at one or more bonding sites.

BRIEF DESCRIPTION OF THE DRAWINGS

FIG. 8 is a schematic cross-sectional view of the web of FIG. 5 taken along line 8-8.

FIG. 9 is a schematic side elevation view of a web in accordance with another nonlimiting embodiment of the present invention.

FIG. 17 is a schematic perspective view of layers of a laminate in accordance with one nonlimiting embodiment of the present invention.

FIG. 18a is a schematic side elevation view of a portion of a laminate in accordance with another nonlimiting embodiment of the present invention.

FIG. 18b is a schematic plan view of layers of a laminate in accordance with a nonlimiting embodiment of the present invention.

FIG. 19 is a schematic side elevation view of a portion of a laminate in accordance with one nonlimiting embodiment of the present invention.

DETAILED DESCRIPTION OF THE INVENTION

Definitions

Figure 1:
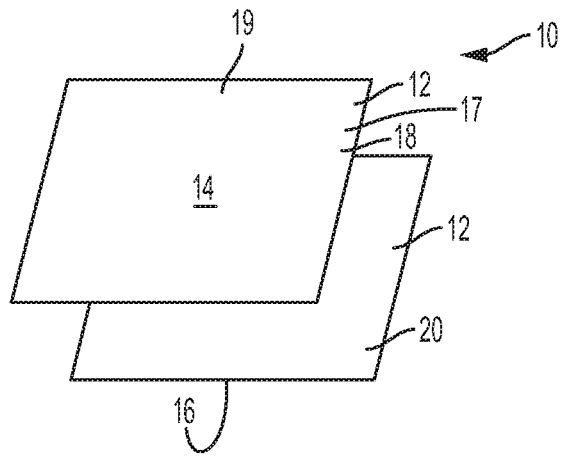
FIG. 1 is a schematic exploded perspective view of a laminate in accordance with one nonlimiting embodiment of the present invention.

"Absorbent article" means a device that absorbs and contains body exudates and, more specifically, devices that are placed against or in proximity to the body of the wearer to absorb and contain the various exudates discharged from the body. Exemplary absorbent articles include diapers, training pants, pull-on pant-type diapers (i.e., a diaper having a pre-formed waist opening and leg openings such as illustrated in U.S. Pat. No. 6,120,487), refastenable diapers or pant-type diapers, incontinence briefs and undergarments, diaper holders and liners, feminine hygiene garments such as panty liners, absorbent inserts, and the like.

"Activation" is the mechanical deformation of a plastically stretchable material that results in permanent elongation of the stretchable material, or a portion of the stretchable material, in the direction of activation in the X-Y plane of the material. For example, activation occurs when a web or portion of a web is subjected to a stress that causes the material to strain beyond the onset of plasticity, which may or may not include complete mechanical failure of the material or portion of the material. Activation of a laminate that includes an elastic material joined to a plastically stretchable material typically results in permanent deformation of the plastic material, while the elastic material returns substantially to its original dimension. "Activate," and variations thereof, means subjecting a material to an activation process. "Pre-activate," and variations thereof, means to activate a component prior to lamination of the component with other layers. Activation processes include incremental stretching and SELFing.

"Activation thickness" means a depth created in a component by activation. An activation thickness is the maximum depth of a deformed area as measured in the z-direction.

"Disposable," in reference to articles, means that the articles are generally not intended to be laundered or otherwise restored or reused in the same capacity (i.e., they are intended to be discarded after a single use and, preferably, to be recycled, composted or otherwise discarded in an environmentally compatible manner).

"Elastic," "elastomeric," and "elastically extensible" mean the ability of a material to stretch by at least 25% without rupture or breakage at a given load, and upon release of the load the elastic material or component exhibits at least 80% recovery (i.e., has less than 20% set). For example, an elastic material that has an initial length of 100 mm can stretch to at least 150 mm (50% stretch) and, upon removal of the force, retract to a length of 110 mm (i.e., have a set of 10 mm or 10%). Stretch, sometimes referred to as strain, percent strain, engineering strain, draw ratio, or elongation, along with recovery and set may each be determined according to the Hysteresis Test described in more detail below. It is to be understood; however, that this definition of elastic does not apply to materials that do not have the proper dimensions (e.g., not wide enough) to be properly subjected to the Hysteresis Test. Instead, such material is considered to be elastic if it can stretch to at least 25% upon application of a biasing force, and return substantially to its original length (i.e., exhibit less than 20% set) upon release of the biasing force. In certain embodiments, a material exhibits less than 20% set when stretched without rupture or breakage by about 50% or more, or about 100% or more, or from about 25% to about 200%. In other words, the material is elastically extensible at a specified strain of about 50% or more, or about 100% or more or from about 25% to about 200%.

"Extensible" means the ability to stretch or elongate, without rupture or breakage, by at least 25%. If a material can undergo the first cycle of the Hysteresis Test described herein (where the specified strain is 25%) without rupture, it is extensible. In certain embodiments herein, a material comprises extensibility when stretched by about 50% or more, or about 100% or more, or from about 25% to about 200%. In other words, the material can undergo the first cycle of the Hysteresis Test without rupture or breakage where the specified strain is about 50% or more, or about 100% or more, or from about 25% to about 200%.

"Film" means a sheet-like material wherein the length and width of the material far exceed the thickness of the material (e.g., 10×, 50×, or even 1000× or more). Films are typically liquid impermeable but may be configured to be breathable.

"Incremental stretching" means a process in which a web material is controllably plastically stretched in increments along one or more directions by being passed under tension between the surfaces of a pair of stretching members having continuously intermeshing ridges and valleys, or other intermeshing features as described for example, in U.S. Pat. Pub. No. 2013/0082418 and U.S. Pat. No. 5,167,897. The stretching members may comprise a pair of rollers (e.g., ring rollers), gear-like rollers, belts or plates with continuously intermeshing features. Ring-rolling is a type of incremental stretching.

"Joined" means configurations whereby an element is directly secured to another element by affixing the element directly to the other element, and configurations whereby an element is indirectly secured to another element by affixing the element to intermediate member(s) that in turn are affixed to the other element.

"Laminate" means two or more materials that are bonded to one another by any suitable method known in the art (e.g., adhesive bonding, thermal bonding, ultrasonic bonding, or high pressure bonding using non-heated or heated patterned roll).

"Longitudinal" means a direction lengthwise in an article such that the longitudinal direction may run parallel to the maximum linear dimension in the x-y plane of the article. In an absorbent article as described herein, the longitudinal direction runs substantially perpendicular from a waist end edge to an opposing waist end edge when the absorbent article is in a flat out, uncontracted state, or from a waist end edge to the bottom of the crotch in a bifolded article. Directions within 45 degrees of the longitudinal direction are considered to be "longitudinal." "Lateral" refers to a direction running from a side edge to an opposing side edge of an article and generally perpendicular to the longitudinal direction. Directions within 45 degrees of the lateral direction are considered lateral.

"Machine direction" or "MD" is the direction parallel to the direction of travel of the web in a manufacturing process. Directions within 45 degrees of the MD are considered to be machine directional. The "cross machine direction" or "CD" is the direction substantially perpendicular to the MD and in the plane generally defined by the web. Directions within 45 degrees of the CD are considered to be cross directional.

"Nonwoven" means a porous, fibrous material made from continuous (long) filaments (fibers) and/or discontinuous (short) filaments (fibers) by processes such as, for example, spunbonding, meltblowing, airlaying, carding, coforming, hydroentangling, and the like. Nonwovens do not have a woven or knitted filament pattern. Nonwovens may be liquid permeable or impermeable.

"Relaxed" means the state of an element, material or component at rest with substantially no external force acting on the element, other than gravity.

"SELF" or "structured elastic-like form" means a process in which a web material is controllably plastically stretched in increments along one or more directions by being passed under tension between the surfaces of a pair of stretching members having discontinuously intermeshing ridges and valleys, or other features as described in, for example, U.S. Pat. No. 5,993,432. The stretching members may be a pair of rollers, gear-like members, belts or plates with discontinuous intermeshing features. Pre-SELF components are subjected to the SELF process prior to lamination to or with other components/layers.

"Unactivated," in reference to a component, means the component as a collective whole has not undergone an activation process. For instance, an unactivated laminate may comprise layers that have been activated, but the laminate as a whole (post-lamination) has not undergone an activation process.

"Web" means a material capable of being wound into a roll. Webs may be films, nonwovens, laminates, apertured films and/or laminates, and the like. The face of a web refers to one of its two dimensional surfaces, as opposed to its edge.

"X-Y plane" means the plane defined by the MD and CD of a moving web or the length and width of a piece of material. The Z-direction is perpendicular to the X-Y plane.

Overview

The present invention relates to elastomeric laminates having one or more layers that have been activated prior to lamination, particularly where the entire laminate is not subjected to activation post-lamination (i.e., the entire laminate is unactivated).

Figure 2:
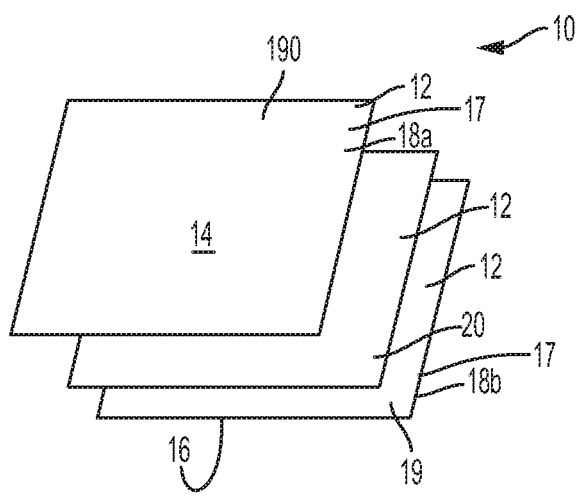
FIG. 2 is a schematic exploded perspective view of a laminate in accordance with another nonlimiting embodiment of the present invention.

The laminate 10 may comprise two or more layers 12, a first surface 14 and a second surface 16 substantially opposite the first surface 14. The laminate further comprises a total thickness, T, which is the greatest z-direction distance between the first surface and the second surface (i.e., the height distance between the highest point on the first surface and the lowest point on the second surface when the laminate is positioned such that its X-Y plane is horizontal). The first and second surfaces 14, 16 may be formed by different layers 12. The laminate layers 12 may comprise at least one coverstock layer 17 and at least one elastomeric layer 20. The coverstock layer 17 may comprise a pre-SELFed coverstock layer 18, where the layer 17 is SELFed prior to lamination. In an embodiment, a first pre-SELFed coverstock layer 18 forms the first surface 14 and a first elastomeric layer 20 forms the second surface 16 of the laminate as shown in FIG. 1. In an alternative embodiment, the first and second surfaces 14, 16 are formed by different coverstock layers (18a, 18b) as shown in FIG. 2. At least one of the coverstock layers 18a is SELFed prior to lamination.

Figure 3A:
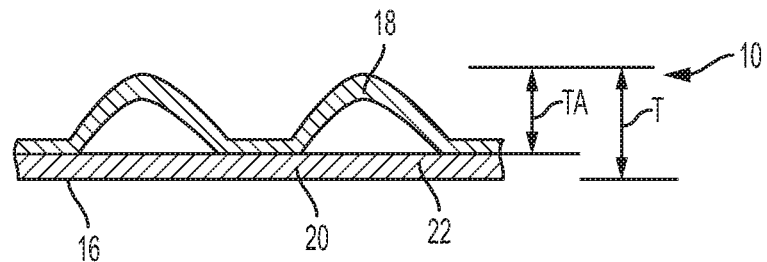
FIGS. 3a-3b are schematic side elevation views of portions of laminates in accordance with nonlimiting embodiments of the present invention.
Figure 3B:
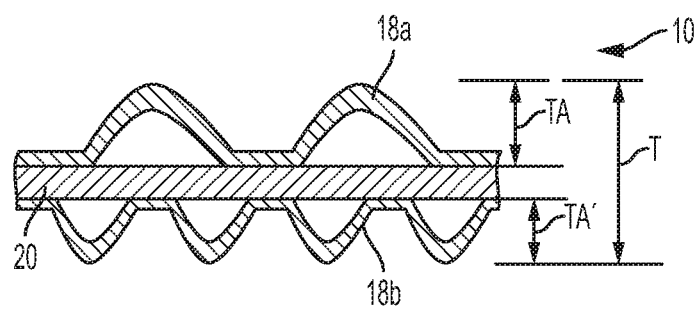
Figure 3C:
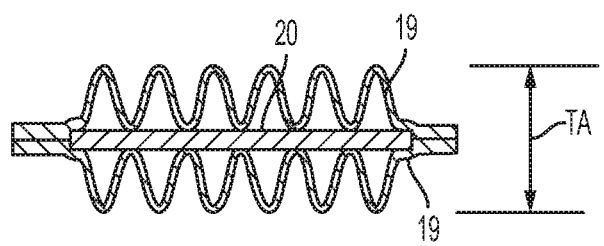
FIG. 3c is a schematic side elevation view of a portion of a prior art laminate.

The SELFing process, as well as other activation processes, creates one or more activation thicknesses, TA. Every activation thickness in a layer that is pre-activated will be less than the total thickness of the laminate, T, as shown in FIGS. 3a and 3b. In other words, the activation thicknesses do not extend through the entire thickness of the laminate. Comparatively, FIG. 3c is an example of a prior art laminate, where the activation thickness does extend through the entire thickness of the laminate.

The Pre-SELFed Coverstock Layer

A coverstock layer 17 is generally non-elastic. Coverstock layer materials 19 may be selected from nonwovens, films and/or any other type of web-based material. In some embodiments, one or more coverstock materials comprise a nonwoven 190. Any suitable nonwoven may be used, including activatable nonwovens. It is typically desirable for the precursor nonwoven web to have extensibility to enable the fibers to stretch and/or rearrange into the form of the protrusions and maintain at least some non-broken fibers in the sidewalls of the protrusions. It may be desirable for the precursor nonwoven to be capable of undergoing an apparent elongation (strain at the breaking force, where the breaking force is equal to the peak force) of greater than or equal to about one of the following amounts: 100% (that is double its unstretched length), 110%, 120%, or 130% up to about 200%. The MD and CD tensile properties are measured using World Strategic Partners (WSP) (harmonization of the two nonwovens organizations of INDA (North American based) and EDANA (Europe based)) Tensile Method 110.4 (05) Option B, with a 50 mm sample width, 60 mm gauge length, and 60 mm/min rate of extension. Note that the gauge length, rate of extension and resultant strain rate are from different from that specified within the method. Activatable nonwovens may comprise polypropylene, polyethylene and combinations thereof.

Figure 4:
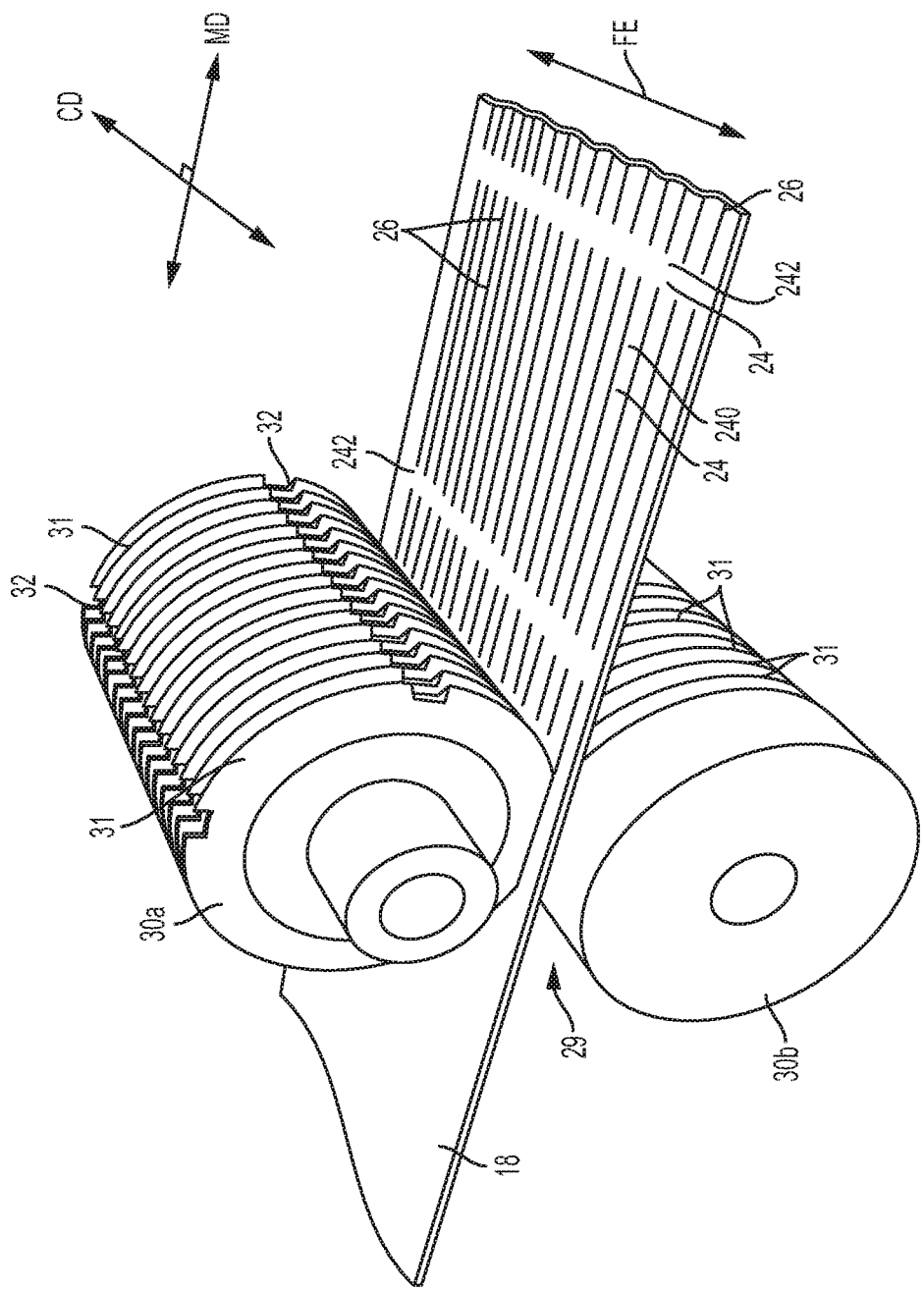
FIG. 4 is a schematic perspective view of an apparatus and process for activating a web material in accordance with one nonlimiting embodiment of the present invention.

In an embodiment, the laminate 10 comprises a first pre-SELFed coverstock layer 18. Prior to being joined to another layer 12, the first pre-SELFed layer 18 or a portion of said layer may be SELFed as defined herein. The layer 18 may be SELFed by any suitable method and/or apparatus. Exemplary methods/apparatuses of SELFing are described in U.S. Pat. Nos. 5,891,544; 5,993,432; 5,968,029 with respect to SELF'ing laminates. However, in the present invention said processes are utilized on the layer 18 prior to lamination. In an embodiment, the coverstock material 18 may be passed through a nip 29 between a pair of rotating SELF'ing rolls 30 as shown in FIG. 4. Each roll may comprise a series of ridges 31, where the ridges on the first roll 30a are offset from the ridges on the second roll 30b. In this way, the ridges intermesh as the web of coverstock material is passed through the nip 29. One or more of the ridges 31 on the first roll 30a and/or the second roll 30b may comprise a plurality of notches 32. The intermeshing ridges plastically deform the material 18, creating deformed areas 26 (shown as lines on the web 18 in FIG. 4). Portions of the web coverstock material 18 are left relative less stretched or substantially intact. These less stretched or substantially intact areas will be referred herein to as land areas 24, which will be separated by the deformed areas 26. Generally, the land areas 24 are regions that experience little or no local straining during activation and therefore, the land areas 24 are regions with little to no localized permanent deformation. On the other hand, the deformed areas 26 experience local strain during activation and therefore have localized permanent deformation. This deformation provides increased extensibility in a first extensibility direction, FE, relative to the web's initial extensibility. The first extensibility direction, FE, is substantially perpendicular to the direction of the ridges 31.

Figure 4A:
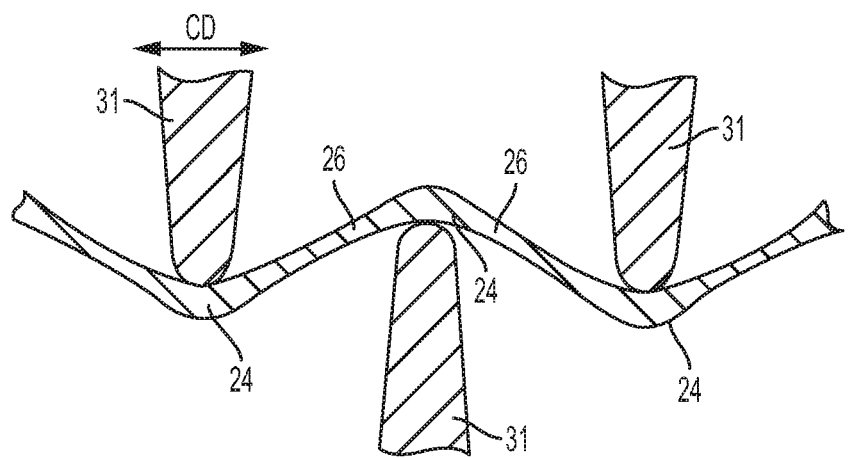
FIG. 4a is a schematic side elevation view of a portion of a web material as it passes through a nip between a pair of stretching members during activation in accordance with one nonlimiting embodiment of the present invention.
Figure 5:
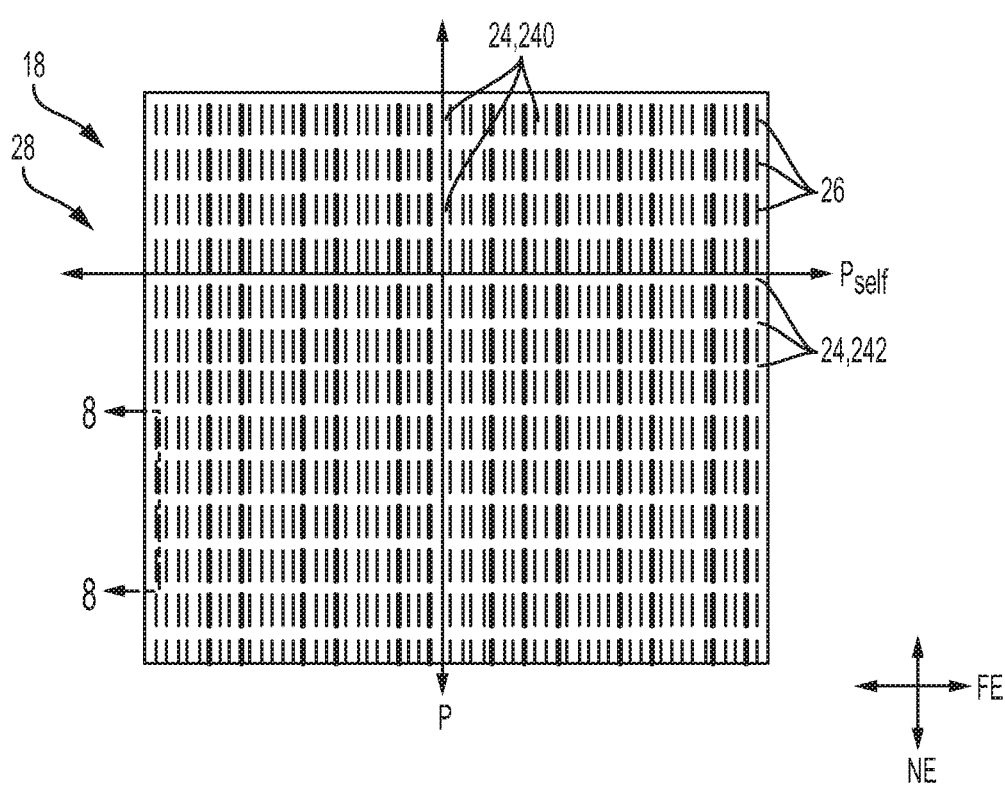
FIG. 5 is a schematic plan view of an activated web material in accordance with one nonlimiting embodiment of the present invention.

In most activation processes (including SELF), land areas 24 coincide with areas of the web 18 that contact the tip of the ridges on the respective rolls as shown in FIG. 4a. (FIG. 4a is a partial side view of a web undergoing activation in an area of the apparatus that does not have notches 32.) Without being bound by theory, it is believed that the web 18 is friction-locked about the tip of the ridge and therefore no deforming force is exerted on the material 18 in that area. Land areas corresponding with areas where the web contacts the tip of the intermeshing ridges will be referred to herein as activation land areas 240. Activation land areas 240 follow a continuous directional path, P, through at least a portion of the web 18. Said path, P, is generally perpendicular to the direction of extensibility of the activated material, as depicted in FIG. 4 and FIG. 5. For purposes of this disclosure, the direction perpendicular to the direction of extensibility will be referred to as the non-extensible direction, NE.

Figure 7:
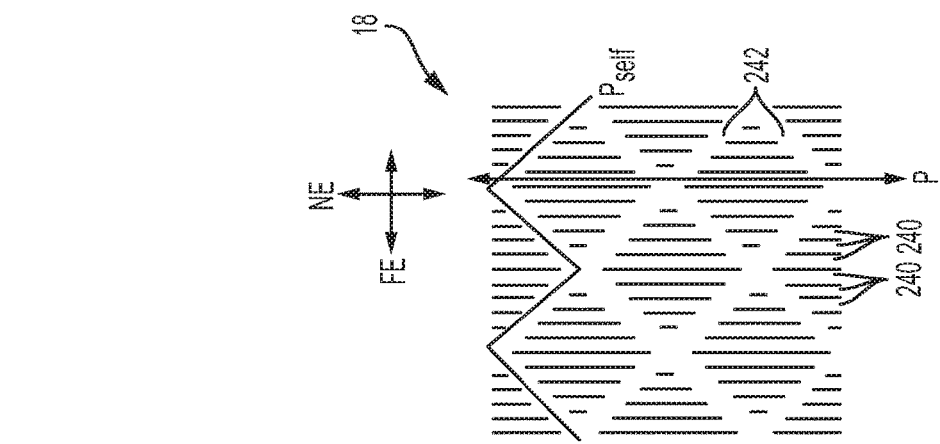
FIG. 7 is a schematic plan view of an activated web material in accordance with one nonlimiting embodiment of the present invention.
Figure 6:
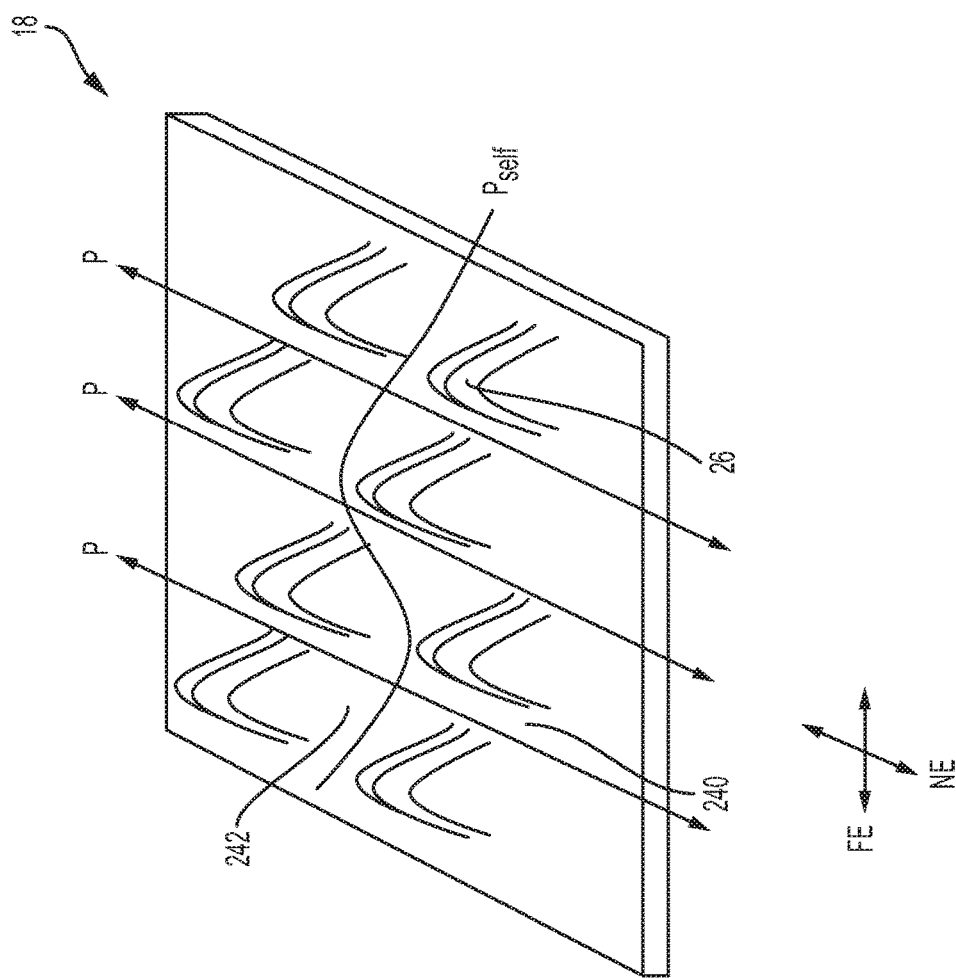
FIG. 6 is a schematic perspective view of a web material after activation in accordance with a nonlimiting embodiment of the present invention.

The SELF process, however, additionally creates SELF-specific land areas 242 which occur when the web 18 encounters or passes the notches 32. SELF-specific land areas 242 will follow a continuous directional path, $P_{self}$, through at least a portion of the web 18. Because the notches 32 are disposed on the intermeshing ridges 31 in the SELF activation process, the path $P_{self}$ is not orthogonal to the direction of extensibility, FE. Rather, the continuous directional path, $P_{Self}$, extends in substantially the same direction as the direction of extensibility. The path, $P_{self}$, may be straight as depicted in FIG. 5, or may curvilinear as shown in FIG. 6 (where, for example, SELF-specific land areas are offset in the CD and/or MD). $P_{self}$ may also be at any non-orthogonal angle relative to the direction of extensibility (for example within about 45 degrees of the direction of extensibility) or zig zag as depicted in FIG. 7. As can be seen in FIGS. 5-7, the paths (P, $P_{self}$) may overlap. Essentially, notches 32 in the SELFing process cause deformed areas in the web to be discontinuous in the non-extensible direction. This lack of continuity in the deformed areas allows for a continuous path of land areas to extend in substantially the same direction as the direction of extensibility. Other activation processes do not provide deformed areas that are discontinuous in the non-extensible direction.

SELFing provides extensibility properties that a traditional activation process cannot provide. The SELF-specific land areas provide additional tailoring of the overall extension properties because said SELF-specific land areas inhibit extension locally. In addition, spacing between notches 32 on the ridges 31 (i.e., the length between two notches on the ridge) may vary, allowing for non-uniform properties (e.g., extensibility) within the web 18. Further, the SELF-specific land areas 242 also contribute to unique three-dimensional textures that are not possible without the notches.

In SELF activation, the notches 32 and intermeshing features 31 may be disposed on the stretching members 30 in a SELF pattern to form patterns of land areas 24 on a material. Exemplary patterns that can be created through SELFing are depicted in U.S. Pat. Nos. USD402,121, USD673,746. The orientation and arrangement of the land areas 24 with respect to the extensibility direction affects the degree of extensibility. For example, a curvilinear or a zigzag $P_{Self}$ as in FIG. 6 or 7 will provide greater extensibility than a substantially straight path, $P_{self}$, in the same web. Likewise, a linear $P_{Self}$ that is narrower (as measured in the nonextensibility direction as the distance between deformed areas) will provide greater extensibility than a linear $P_{Self}$ that is wider, and a linear $P_{self}$ disposed at an angle with respect to the direction of extensibility will provide greater extensibility than a linear $P_{self}$ that is parallel to the direction of extensibility. By greater extensibility, it is meant that a material will elongate without rupture at greater levels of strain.

Turning to FIGS. 8-9, the pre-SELFed layer 18 may comprise one or more activation thicknesses, TA. Where layer comprises multiple activation thicknesses, those thicknesses may vary in dimensions. Additionally or alternatively, some activation thicknesses may have the same dimensions. Variation in multiple activation thicknesses may arise in the MD and/or in the CD. Importantly, all of the activation thicknesses, TA, will be less than the total thickness of the laminate 10.

In an embodiment, the pre-SELFed coverstock layer 18 comprises a primary activation pattern 28. The primary activation pattern 28 includes SELF-specific land areas 242 that follow a continuous directional path, $P_{self}$, in the first extensibility direction, FE. In one nonlimiting example, the first extensibility direction, FE, is substantially the same as the cross machine direction.

The activation pattern 28 may comprise a uniform design 28a in MD and/or in the CD. In one nonlimiting example, the notch-to-notch spacing in one or more directions on the stretching members 30 may be uniform resulting in substantially uniform spacing of the SELF-specific land areas 242 in one or more directions as shown in FIG. 8. In a further nonlimiting example, the remaining activation land areas 240 may be uniformly spaced. Additionally or alternatively, in a uniform pattern 28a, activation thicknesses corresponding to SELF-specific land areas and/or activation thicknesses corresponding to non SELF-specific land areas may be the same.

Figure 10:
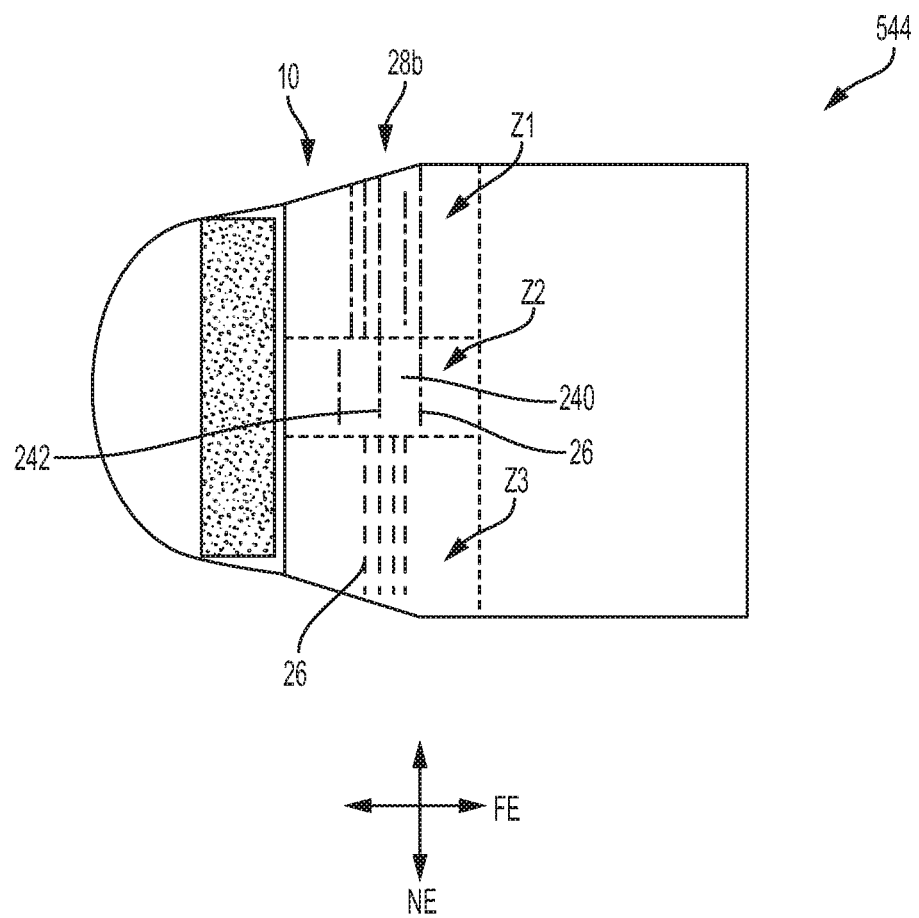
FIG. 10 is a schematic plan view of a fastener in accordance with one nonlimiting example of the present invention.

In another nonlimiting example, the activation pattern 28 is non-uniform in the X-Y plane and/or in the z-direction. An exemplary non-uniform pattern 28b is shown in FIG. 9 where the deformed areas comprise different z-direction heights. Additionally or alternatively, a non-uniform pattern 28b may comprise varied spacing in the MD and/or CD as shown in FIG. 10. (FIG. 10 is a schematic representation of a fastener 544 with zones delimited by dotted lines.) Non-uniform patterns 28b may be particularly useful where differential properties are desired within the layer. For instance, a non-uniform pattern may create differential modulus resulting from deformed areas 26 being disposed inconsistently throughout the pattern 28b. FIG. 10 provides a non-limiting example of this concept by illustrating different designs rendering differential modulus (and/or other properties) between zones Z1, Z2, and Z3. A non-uniform pattern 28b may also create differing aesthetics throughout the pattern 28b, which may result in a desirable design.

The Elastomeric Layer

The laminate 10 further comprises an elastomeric layer 20. The elastomeric layer 20 comprises one or more elastomeric materials 22 which provide elasticity to at least a portion of the layer 20. Nonlimiting examples of elastomeric materials 22 include film (e.g., polyurethane films, films derived from rubber and/or other polymeric materials), elastic strands (e.g., LYCRA® strand, natural and/or synthetic rubber), an elastomeric coating applied to another substrate (e.g., a hot melt elastomer, an elastomeric adhesive, printed elastomer or elastomer co-extruded to another substrate), elastomeric nonwovens, scrims. Elastomeric materials can be formed from elastomeric polymers including polymers comprising styrene derivatives, polyesters, polyurethanes, polyether amides, polyolefins, combinations thereof or any suitable known elastomers including but not limited to co-extruded VISTAMAXX®. Exemplary elastomers and/or elastomeric materials are disclosed in U.S. Pat. Nos. 8,618,350; 6,410,129; 7,819,853; 8,795,809; 7,806,883; 6,677,258 and U.S. Pat. Pub. No. 2009/0258210. Commercially available elastomeric materials include KRATON (styrenic block copolymer; available from the Kraton Chemical Company, Houston, Tex.), SEPTON (styrenic block copolymer; available from Kuraray America, Inc., New York, N.Y.), VECTOR (styrenic block copolymer; available from TSRC Dexco Chemical Company, Houston, Tex.), ESTANE (polyurethane; available from Lubrizol, Inc, Ohio), PEBAX (polyether block amide; available from Arkema Chemicals, Philadelphia, Pa.), HYTREL (polyester; available from DuPont, Wilmington, Del.), VISTAMAXX (homopolyolefins and random copolymers, and blends of random copolymers, available from EXXON Mobile, Spring, Tex.) and VERSIFY (homopolyolefins and random copolymers, and blends of random copolymers, available from Dow Chemical Company, Midland, Mich.).

Figure 11:
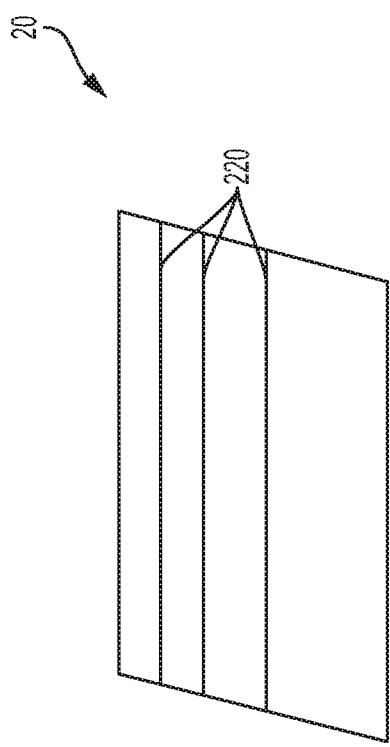
FIG. 11 is a schematic perspective view of an elastomeric layer in accordance with one nonlimiting embodiment of the present invention.
Figure 12B:
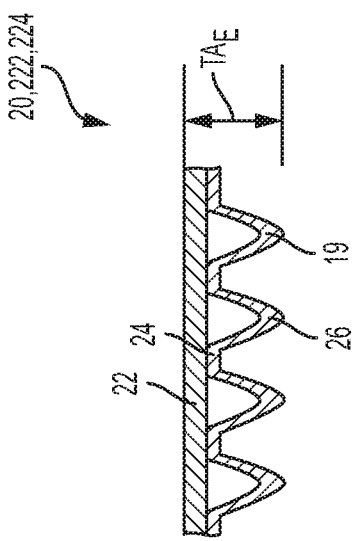
FIG. 12b is a schematic side elevation view of a portion of an elastomeric laminate layer in accordance with one nonlimiting embodiment of the present invention.
Figure 12A:
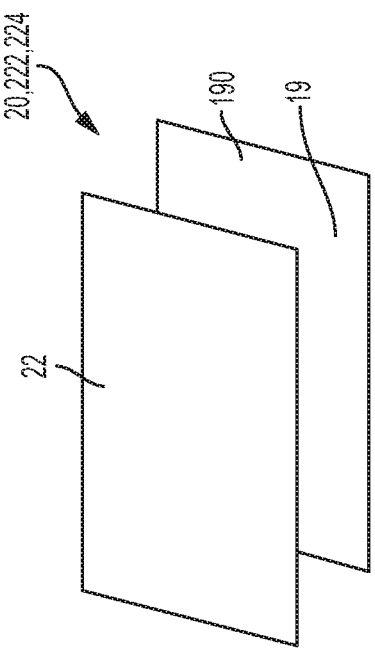
FIG. 12a is a schematic, exploded perspective view of an elastomeric laminate layer in accordance with one nonlimiting embodiment of the present invention.

In an embodiment shown in FIG. 11, the elastomeric layer 20 comprises an inherently elastomeric material 220. Non-limiting examples of inherently elastomeric materials include rubber and stretchable films or filaments (e.g., SPANIDEX®, LYCRA®). In another embodiment, the elastomeric layer 20 comprises an activated elastomeric material 222 (i.e., a material that becomes elastomeric or enhances its elasticity through activation) as shown in FIGS. 12a-12b. The activated elastomeric material 222 is activated prior to being joined to the pre-SELFed layer 18.

In a further embodiment, the elastomeric layer 20 may comprise an elastomeric laminate layer 224. The elastomeric laminate layer 224 may comprise two elastomeric materials 22 joined together (e.g., two inherently elastomeric materials 220 joined together). As shown in FIGS. 12a and 12b, the elastomeric laminate layer 224 may comprise an elastomeric material 22 joined to a coverstock material 19 (e.g., a nonwoven 190) and subsequently activated to form an activated elastomeric material 222.

Figure 13A:
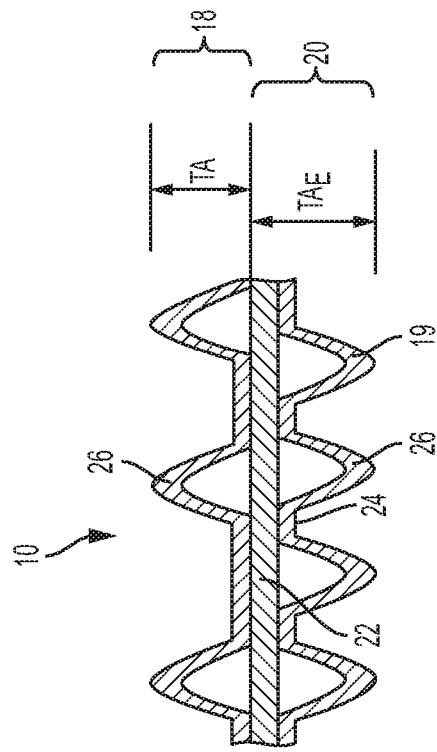
FIGS. 13a-13c are schematic side elevation views of portions of laminates in accordance with nonlimiting embodiments of the present invention.
Figure 13B:
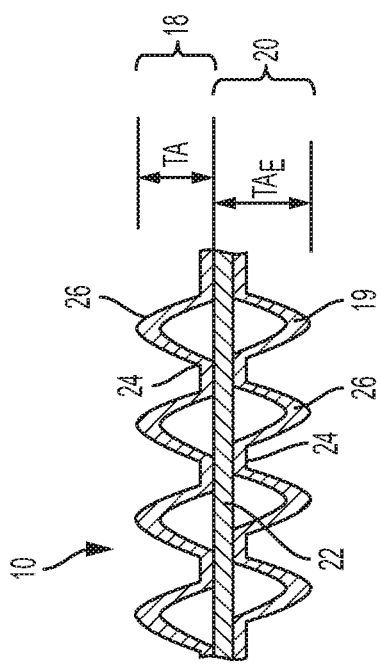
Figure 13C:
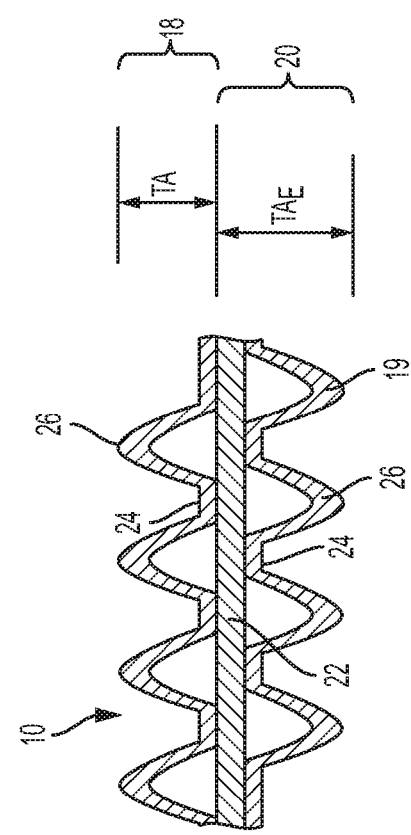

In embodiments involving activated elastomeric materials, said activation forms one or more elastomeric layer activation thicknesses, $TA_E$. The activated elastomeric material 222 may be activated by any suitable means. In one nonlimiting example, the activated elastomeric material 222 undergoes a ring-rolling process (as described in more detail below). In another nonlimiting example, the activated elastomeric material 222 undergoes a SELF process. In such nonlimiting example, the SELF pattern utilized may be the same or it may be different from the SELF pattern utilized on the pre-SELFed coverstock layer 18. In a further nonlimiting example, the deformed areas and/or land areas of an activated elastomeric layer 222 may be at least partially aligned, or substantially fully aligned, with the deformed areas and/or land areas of the pre-SELFed coverstock layer 18 as shown in FIG. 13a. In another nonlimiting example, there may be a random association of land areas and deformed areas between the layers 18, 20 as shown in FIG. 13b. In an alternative nonlimiting example, the land areas and deformed areas of the respective layers may be offset as shown in FIG. 13c.

In some embodiments, the laminate 10 may comprise activation thickness(es) on two different layers—at least one activation thickness, TA, formed on the pre-SELFed coverstock layer 18 and at least another activation thickness, $TA_E$, formed on the elastomeric layer. None of the activation thicknesses (TA, $TA_E$) extend throughout the total thickness, T, of the laminate 10. Said differently, each activation thickness is less than the total thickness.

Additional Layers

The laminate may include more than two layers 12. In one nonlimiting example (discussed above), the elastomeric layer 20 may comprise multiple layers that have been joined together prior to the elastomeric layer 20 being joined with the pre-SELFed coverstock layer 18. In other embodiments, additional layers 12 may include additional elastomeric layers 20 and/or added coverstock layers 17. Each additional layer 12 may be inherently extensible or activated, provided that at least one layer in the laminate is pre-SELFed and that the laminate comprises an activation thickness, TA, that is less than the total thickness of the laminate, T. The additional layers 12 may be used to optimize the total strength, extensibility and/or other functionalities of the laminate 10. In one nonlimiting example, two or more separate coverstock layers 17 may be added to one or both sides of the stretchable material. In this way, additional strength and/or texture may be provided to the laminate 10.

Figure 14:
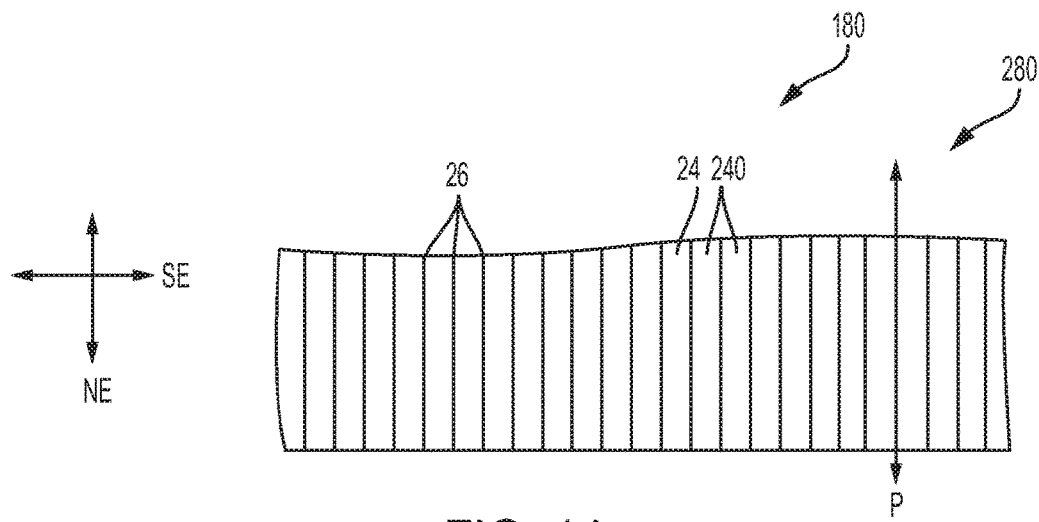
FIG. 14 is a schematic plan view of an activated web material in accordance with one nonlimiting embodiment of the present invention.

In one nonlimiting example, the laminate comprises a pre-SELFed coverstock layer 18 and a second pre-activated coverstock layer 180. The first surface 14 of the laminate may be formed by the pre-SELFed coverstock layer 18 and the second surface 16 may be formed by second pre-activated coverstock layer 180. The second pre-activated coverstock layer 180 may be extensible in a second extensibility direction, SE. The second extensibility direction, SE, may be the same as or different than the first extensibility direction, FE. An exemplary second pre-activated coverstock layer is depicted in FIG. 14. In some embodiments, the degree of extensibility in the pre-SELFed layer differs from the degree of extensibility of the second pre-activated layer 180 in one or more directions.

Figure 15:
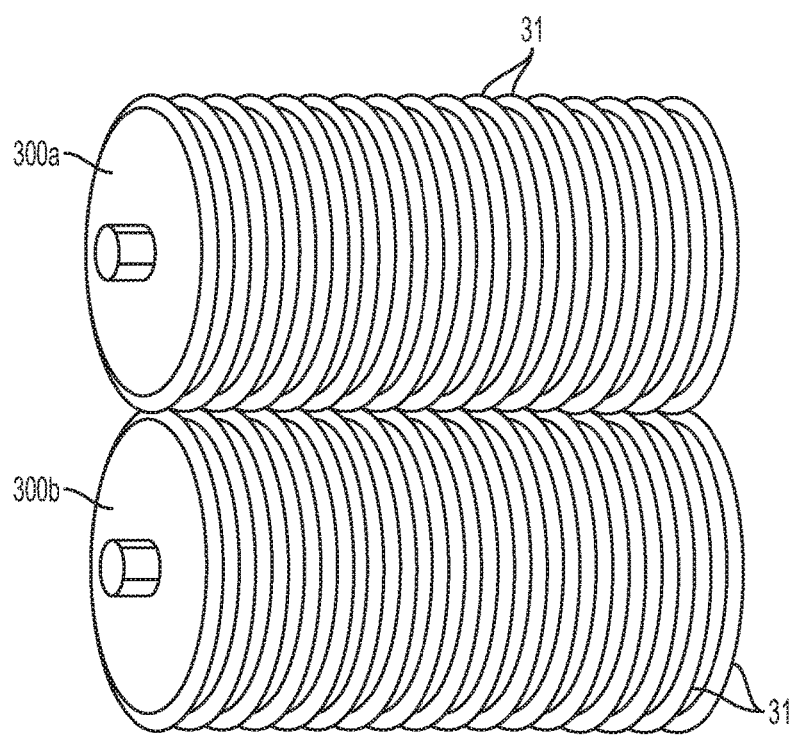
FIG. 15 is a schematic perspective view of an apparatus for activating a web material in accordance with one nonlimiting embodiment of the present invention.

The second pre-activated layer 180 may comprise a secondary activation pattern 280. The secondary activation pattern 280 may be formed by any suitable means of activation. In an embodiment, the second pre-activated coverstock layer 180 is activated by ringrolling (see FIG. 14 showing a ring rolled web and FIG. 15 depicting ring rolling equipment). Ring-rolling typically comprises stretching members with continuously intermeshing features (e.g., intermeshing ridges 31). Compared to the above-described SELF'ing embodiment, the intermeshing features of stretching members (shown as rollers 300a, 300b in FIG. 15) in a ring-rolling process are void of notches 32. In this way, the intermeshing features continuously intermesh the web 180 (e.g., ridges), resulting in deformed areas and activation land areas. As discussed above, the activation land areas 240 will not follow a continuous path in the direction of extensibility of the layer 180. Rather, the activation land areas 240 will typically follow a continuous path in the non-extensible direction, NE.

Figure 16A:
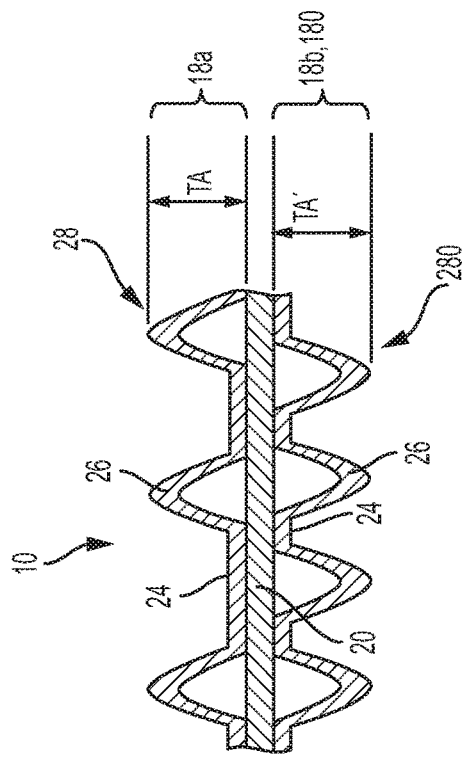
FIGS. 16a-16d are schematic side elevation views of portions of laminates in accordance with nonlimiting embodiments of the present invention.
Figure 16B:
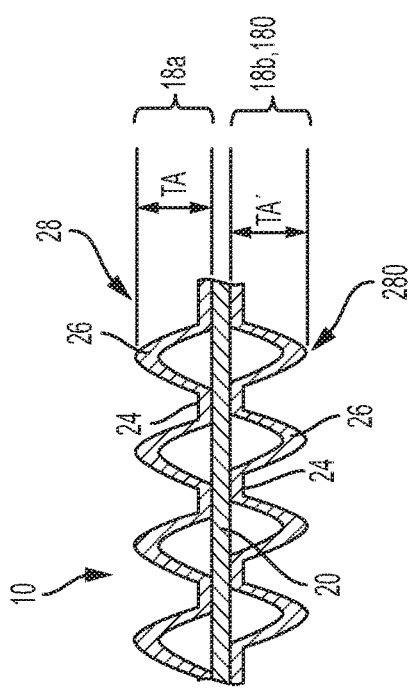
Figure 16C:
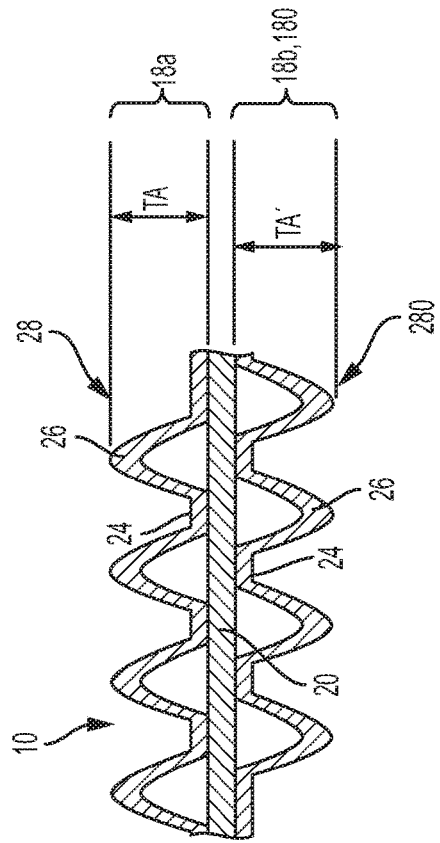

In an alternative embodiment, the second pre-activated coverstock layer 180 comprises a second pre-SELFed coverstock layer 18b, such that the laminate 10 comprises two pre-SELFed coverstock layers 18, 18b and one or more elastomeric layers 20 sandwiched between said pre-SELFed coverstock layers 18a, 18b. In such nonlimiting example, the SELF pattern utilized on the second pre-SELFed coverstock layer 18b may be the same or it may be different from the SELF pattern utilized on the first pre-SELFed coverstock layer 18a. In a further nonlimiting example, the deformed areas and/or land areas of the second pre-SELFed coverstock layer 18b may be at least partially aligned, or substantially fully aligned, with the deformed areas and/or land areas of the first pre-SELFed coverstock layer 18a as shown in FIG. 16a (showing partial alignment). In another nonlimiting example, there may be a random association of land areas and deformed areas between the layers 18a, 18b as shown in FIG. 16b. In an alternative nonlimiting example, the land areas and deformed areas of the respective layers may be offset as shown in FIG. 16c. As explained above, SELF-specific land areas 242 coincide with notches 32 on a stretching member and therefore can follow a continuous directional path in substantially the same direction as the direction of extensibility, SE, for at least a portion of the second pre-SELFed coverstock layer 18b. The secondary pattern 280 formed on a second pre-SELFed coverstock layer 18b may also comprise activation land areas 240 that do not follow a continuous directional path in the second extensibility direction, SE. Similar to the first pre-SELFed layer, a second pre-SELFed layer 18b may comprise a uniform design in MD and/or in the CD, a non-uniform design in the MD and/or the CD or combinations thereof. Any suitable SELF pattern may be utilized.

The second pre-activated layer 180 may comprise one or more second activation thicknesses, TA', as illustrated in FIGS. 16a-d. The second activation thickness, TA', may be the same as or may be different than one or more activation thicknesses, TA, in the first pre-SELFed coverstock layer 18.

The primary activation pattern 28 and the secondary activation pattern 280 may be the same. Alternatively, the primary pattern and the secondary pattern may differ by: the shape of the land areas, shape of the deformed areas, size of the land areas, size of the deformed areas, number of land areas, type of land areas (i.e., activation, SELF-specific), number of deformed areas, location of land areas, location of deformed areas, pattern uniformity, or combinations thereof.

Each pattern 28, 280 results in certain extensibility capability in the longitudinal and lateral directions of the laminate and certain strength (e.g., extension force, tear strength). When the laminate 10 comprises both patterns 28, 280, a combination of properties from the two patterns is obtained. Said combination is not obtainable from the individual patterns used alone. Further, even offsetting the same pattern on one laminate surface relative to the other surface can create different properties in different sections of the laminate. The ability to create differential properties in the laminate is furthered by non-uniform patterns or two or more patterns disposed on one layer. Nonlimiting examples of creating differential properties by varying activation patterns in areas of a laminate are disclosed in U.S. Pat. Nos. 8,858,523; 8,598,407; 8,568,382 and U.S. Pat. App. Nos. 2007/0142815 and 2007/0287982 A1.

Figure 16D:
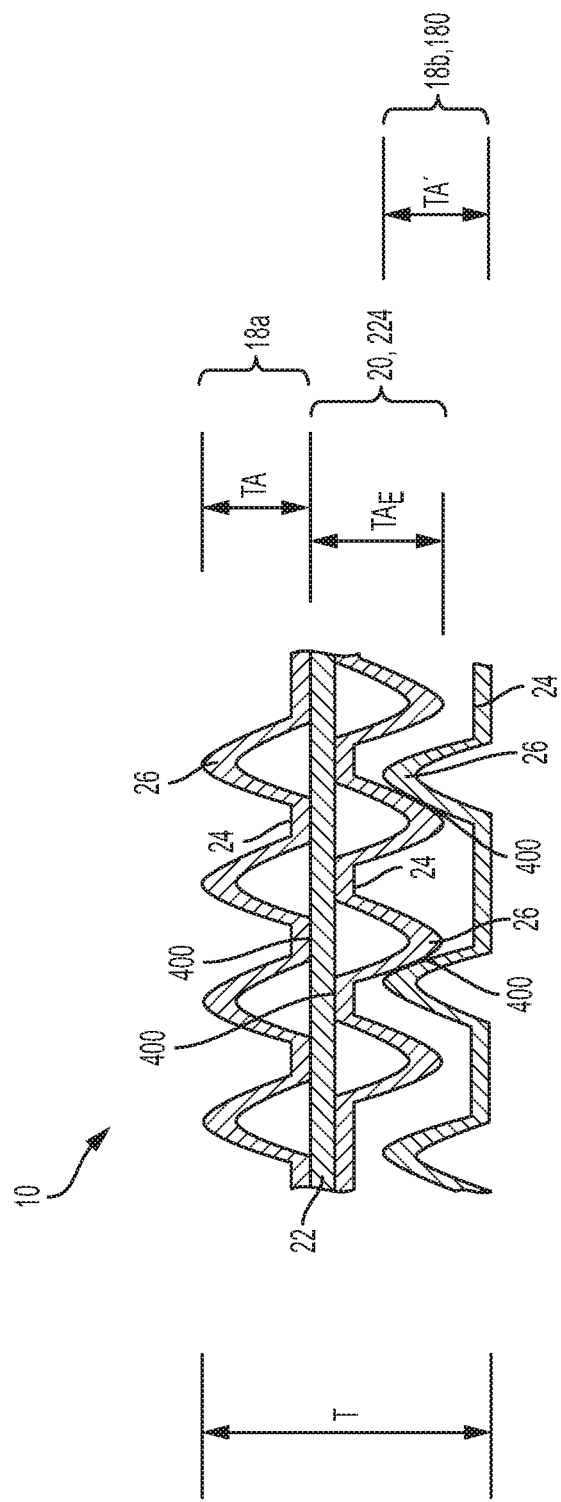

Further, in another embodiment shown in FIG. 16d, the laminate 10 may comprise a first pre-SELFed coverstock layer 18, an activated elastomeric laminate layer 222 and a second pre-activated layer 180, each layer having an activation thickness (TA, $TA_E$, TA') that is less than the total thickness of the laminate, T.

The land areas and/or deformed areas in the various layers 12 may be partially aligned, substantially fully aligned, offset, randomly associated or a combination thereof. Activation thicknesses within a layer may be the same or different. Activation thickness in one layer 12 may be the same as or different from an activation thickness in another layer 12. Moreover, deformed areas 26 may be oriented outwardly as shown for example in layer 18a in FIG. 16d or inwardly as shown in layer 18b in the same Figure. Any workable combination of inwardly and outwardly oriented deformed areas are within the scope of the present disclosure. In some embodiments, both outermost layers comprise outwardly facing deformed areas (i.e., the apex of the deformed area faces away from the interior of the laminate). Outwardly facing deformed areas may provide desirable textures and/or designs.

Laminate

The laminate 10 is formed by joining the various layers 12. The layers 12 may comprise the same dimensions (e.g., area, length, width, shape) or one or more different dimensions. In one embodiment shown in FIG. 17, the laminate is a zero strain laminate 100, wherein the layers 12 are joined while under substantially the same strain levels, or having strain levels that differ by about 5% or less, or about 2% or less. For example, the first layer 12 may comprise a first strain, $\varepsilon_1$, and the second layer 12 may comprise a second strain, $\varepsilon_2$; the first and second strain levels may differ by about 5% or less at the time of lamination. In other words, the layers 12 are laminated at near zero relative strain. In one nonlimiting example, each layer 12 is in relaxed state during lamination, thus forming a zero strain laminate 100.

In additional embodiments shown in FIGS. 18a-18b, the laminate comprises a gathered laminate 200, wherein one of the layers 12a is strained to a greater degree than a remaining layer 12 during lamination. Stated differently, the strained layer 12a may comprise a first strain, $\varepsilon_1$, and the remaining layer 12b may comprise a second strain, $\varepsilon_2$. At the time of lamination, the first strain may be greater than the second strain. In this way, the less stretchable layer (e.g., the coverstock layer 17) will form gathers when the laminate 10 is in a relaxed state. A layer 12a may be strained more than another by, for example, elongating the layer 12a. In one nonlimiting example, the strained layer 12a comprises an elastomeric layer 20. In another nonlimiting example, the strained layer 12a comprises the coverstock layer 17, including for example the pre-SELFed coverstock layer 18. The straining of the coverstock layer causes necking. Regardless of whether the strained layer 12a comprises an elastomeric layer 20 or a coverstock layer 17, corrugations will form in the coverstock (nonelastomeric) layer when the subsequently formed laminate 200 is in a relaxed state.

In yet another embodiment shown in FIG. 19, the laminate 10 may comprise a hybrid gathered laminate 300. The hybrid laminate 300 may comprise two or more layers joined at zero relative strain to form a zero strain laminate 100 which is subsequently joined with one or more layers 12 in the way that a gathered laminate is formed. The zero strain laminate 100 may be activated prior to lamination with another layer. In one nonlimiting example, the zero strain laminate 100 comprises an elastomeric laminate layer 224. In still another nonlimiting example, the zero strain laminate 100 comprises a laminate of a coverstock layer 17 and an elastomeric layer 20. In a further nonlimiting example, the strained layer 12a comprises the zero strain laminate 100. In another nonlimiting example, the strained layer 12a comprises the one or more layers 12 to which the zero strain laminate 100 is joined. In either of the two preceding nonlimiting examples, the non-elastomeric (or less stretchable layer) will form gathers after lamination.

The layers 12 of the laminate 10 may be joined by any suitable means including but not limited to bonding by adhesive, thermal bonds, ultrasonic bonding, pressure bonding and/or other mechanical attachment. The layers 12 may be joined at one or more bond sites 400. In an embodiment, two or more of the laminate layers 12 are joined by uniformly bonding, where the bond sites are evenly and/or regularly distributed throughout any area or the entire laminate. Alternatively, or in addition, two or more laminate layers 12 may be joined by nonuniform bonding where the bond sites 400 are distributed in greater concentrations in certain regions, possibly resulting in differential modulus and/or preventing debonding of the layers especially along the edges. In a further embodiment, one or more bond sites 400 may be aligned with a pattern 28, 280 and/or with one or more land areas 24, and/or with one or more deformed areas 26. Alignment can be achieved by any suitable means known in the art including but not limited to registration.

The laminate is extensible in one or more directions. The laminate is extensible in the first extensibility direction, FE. The laminate may be extensible in the second extensibility direction, SE, as well. The degree of extensibility in the first direction may vary from the degree of extensibility in the second direction. In some embodiments, the second extensibility direction, SE, is caused by additional layers (i.e., the first extensibility direction is due to the properties of a first layer and the second extensibility direction is due to the properties of a second layer). In such embodiments, the first and second extensibility directions may be the same or may differ. In one nonlimiting example, the first extensibility direction, FE, is from about 10° to about 110°, or from about 45° to about 90° with respect to the second extensibility direction, SE, reciting for each range every 5° interval therein. The surfaces 14, 16 of the laminate may comprise patterns of land areas 28, 280. Land areas within the patterns may follow continuous directional paths in the same direction or different directions. One or more of the patterns 28, 280 may comprise land areas that follow a continuous directional path in substantially the same direction as a direction of extensibility FE, SE.

In some embodiments, the laminate 10 is extensible when stretched by about 50% or more, or about 100% or more, or from about 25% to about 200%. In other words, the laminate can undergo the first cycle of the Hysteresis Test described herein without rupture or breakage where the specified strain is about 50% or more, or about 100% or more, or from about 25% to about 200%, reciting for each range every 10% increment therein.

The laminate 10 is elastomeric through at least a portion of its area. In some embodiments, the entire lateral dimension of the laminate is elastomeric. In other embodiments, a portion of at least one edge is non-elastomeric; in this way, said edge of the laminate 10 or laminate layer 12 can be more effectively secured to other portions of the product, in order to prevent debonding over time.

The laminate 10 comprises a total laminate thickness, T, measured as the greatest z-directional distance from the first surface 14 to the second surface 16. The laminate 10 also comprises one or more activation thicknesses, TA, which correspond to the depths created by activating one or more layers 12 as discussed in detail above. Each activation thickness, TA, is less than the total laminate thickness, T. The laminate 10 is not activated once all layers 12 are assembled and joined into the final laminate 10, as doing so would destroy or damage existing land areas 24 and undermine the benefits of layer-specific activation and thicknesses.

Typically, laminates are activated post-lamination and therefore each layer is affected by the activation process, which can lead to several undesirable issues. For instance, elastomeric layers 20 (which may lack the strength of coverstock layers 17) may be damaged in the process.

Likewise, localized defects or properties differences within one or more layers can cause stress risers that, during activation, may lead to undesired weaknesses and/or tears in the final laminate. The more layers being activated, the greater the probability that a stress riser will cause a weakness/tear in one or more locations or layers of the laminate. Further, a defect will be concentrated in a specific location through the depth of the entire laminate, making the laminate weaker. Further still, because the pattern of activation through each layer is identical, designing the desired overall performance (e.g., areas of stretch, areas of strength) of the laminate is limited by the selected pattern. Moreover, while activation can create a texture in a pattern, in some executions, the pattern on the first surface of the laminate may be the inverse (i.e., mirror image) of the pattern of the second surface. As such, areas lacking in softness or cushion on one surface will likewise lack softness/cushion on the opposite surface.

The present invention avoids one or more of these issues. By activating layers separately, fewer layers are activated at once, reducing the likelihood of stress risers and localized defects concentrated throughout the depth of the laminate and/or providing the ability to optimize activation process conditions for each layer (e.g., matching process conditions to material types). Further, the present invention permits a greater degree of freedom in selecting activation patterns for different layers of the laminate, which in turn leads to enhanced customization to achieve desired benefits. The pattern on one surface 14 of the laminate does not have to be the inverse of the pattern on the second surface 16. Thus, for example, the pattern on the first surface 14 may comprise areas of z-directional loft coinciding with areas of low caliper on the opposite surface 16 (the areas of low caliper resulting from the pattern selected for the second surface 16). Likewise, each surface can comprise textures that can be varied in specific areas to enhance comfort for users. Moreover, varying the textures between layers can result in differential modulus in targeted regions. In addition, differential modulus can be made to follow targeted pathways in a given product by using different activation (e.g., SELF) patterns in different locations of the product and/or laminate as discussed above. Layer-specific activation allows more effective balance of strength, modulus, extensibility and texture in the laminate.

In addition, pre-SELFing the coverstock layer 18 allows for more complex textural designs even in gathered laminates, which typically comprise gathers as the single signature look. With the present invention, the pre-SELFed coverstock layer 18 and/or second pre-activated layer 180 may comprise three-dimensionally patterned material that is then gathered on the laminate. Said three-dimensional pattern can create aesthetically pleasing and/or functional variation (e.g., strength, modulus, extensibility). Further, unlike known gathered laminates, a gathered laminate 200 of the present invention can achieve extensibility levels that are not contingent on the amount of coverstock material used. The amount of stretch in a traditional gathered laminate is directly linked to the length of the coverstock layer. For example, if the laminate is expected to stretch twice the length of its relaxed length, then the coverstock material layer must be about twice the length of the elastomeric layer. Here, however, activation permits greater stretch without using as much coverstock material.

Articles

A laminate in accordance with the present disclosure may be utilized in various articles, including but not limited to stretchable bandages, stretchable body wraps and shape wear, packaging materials and absorbent articles. In some embodiments, an article comprising the laminate 10 is disposable. In some embodiments, a disposable absorbent article comprises the laminate 10. In still further embodiments, more than one laminate 10 is used in a single article. In such embodiments, the laminates 10 may have the same or different properties.

Figure 20:
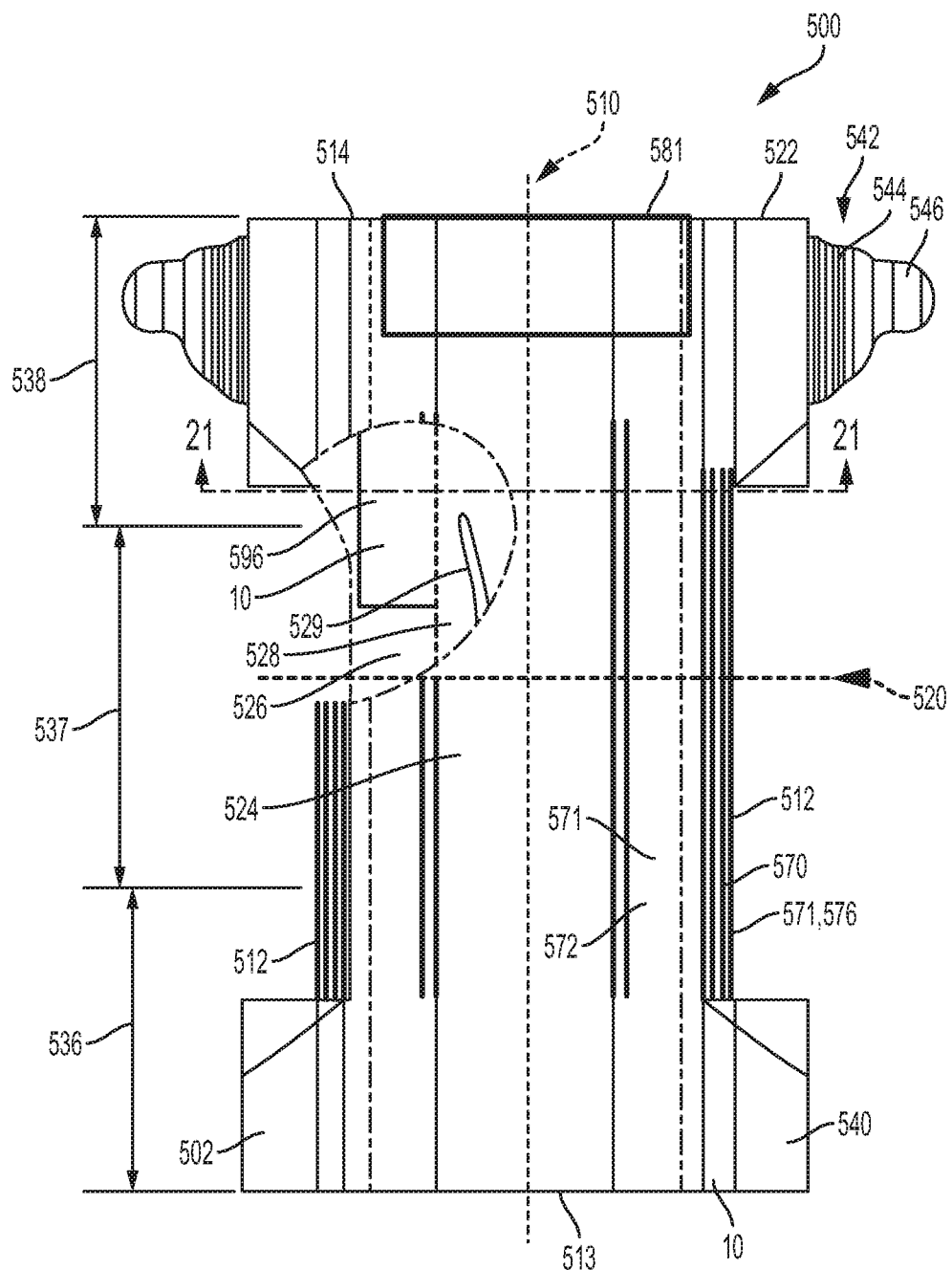
FIG. 20 is schematic plan view of an exemplary absorbent article according to one nonlimiting embodiment of the present invention. The absorbent article is shown in a flat, uncontracted state.

FIG. 20 is a plan view of an exemplary, non-limiting embodiment of an absorbent article 500 of the present invention in a flat, uncontracted state. The body-facing surface 502 of the absorbent article 500 is facing the viewer. The absorbent article 500 includes a longitudinal centerline 510 and a lateral centerline 520, two longitudinal edges 512, and a front waist edge 513 opposite a back waist edge 514. The absorbent article 500 comprises a chassis 522. The absorbent article 500 and chassis 522 are shown to have a first waist region 536, a second waist region 538 opposed to the first waist region 536, and a crotch region 537 located between the first waist region 536 and the second waist region 538. The waist regions 536 and 538 generally comprise those portions of the absorbent article 500 which, when worn, encircle the waist of the wearer. The crotch region 537 is the portion of the absorbent article 500 which, when the absorbent article 500 is worn, is generally positioned between the legs of the wearer.

The chassis 522 may comprise a liquid permeable topsheet 524, a backsheet 526, and an absorbent core 528 between the topsheet 524 and the backsheet 526. The topsheet 524 may be joined to the core 528 and/or the backsheet 526. The backsheet 526 may be joined to the core 528 and/or the topsheet 524. It should be recognized that other structures, elements, or substrates may be positioned between the core 528 and the topsheet 524 and/or backsheet 526, including but not limited to an acquisition-distribution system. In certain embodiments, the chassis 522 comprises the main structure of the absorbent article 500 with other features added to form the composite absorbent article structure. While the topsheet 524, the backsheet 526, and the absorbent core 528 may be assembled in a variety of well-known configurations, absorbent article configurations are described generally in U.S. Pat. Nos. 3,860,003; 5,151, 092; 5,221,274; 5,554,145; 5,569,234; 5,580,411; and 6,004, 306. Additional nonlimiting examples of suitable configurations are described in U.S. Pat. Nos. 5,575,783; 5,242,436; 5,499,978; 5,507,736; and 5,368,584.

The laminate 10 may be joined to the chassis 522 and/or may be a portion of a component that is joined to the chassis 522. The laminate 10 may be disposed in one of the first waist region, second waist region, and/or crotch region. Nonlimiting examples of components comprising the laminate include a side panel (such as an ear 542), a leg cuff 571, elastic waist feature 581 and a hip panel 596.

In some embodiments, the laminate 10 can be used to provide stretch and the aforementioned benefits in the chassis 522. At least a portion of the topsheet 524 and/or at least a portion of the backsheet 526 may comprise a laminate 10 of the present invention in order to provide stretch to the chassis. In one nonlimiting example, a coverstock material such as a nonwoven is pre-SELFed in accordance with the present disclosure and subsequently joined to a stretchable material to form a laminate 10 which is then incorporated into or becomes a portion of the topsheet 524 or a portion of the backsheet 526.

In some embodiments, a portion of the backsheet 526 and/or portion of the topsheet 524 may be used as a part of the laminate 10. In such case, said portion of the backsheet 526 and/or said portion of the topsheet 524 may comprise a coverstock layer 17. In one nonlimiting example, the coverstock layer 17 comprises the backsheet 526, in particular an outer cover 526a of the backsheet 526. In such nonlimiting example, the elastomeric layer 20 may superpose the entire outer cover or a portion of the outer cover. Further, in such embodiments, the core 528 may be within, over or under the laminate 10 but unattached to the elastomeric layer. In this way, stretch is not limited by the materials within the core, allowing greater stretch and conformity to the wearer's body. An exemplary manner of attaching the core to avoid interference with stretch laminates is disclosed in U.S. Pat. Nos. 8,124,828, 8,569,571, and 5,575,783.

Topsheet:

The topsheet 524 may be positioned at least in partial contact or close proximity to a wearer. Suitable topsheets 524 may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. The topsheet 524 is generally supple, soft feeling, and non-irritating to a wearer's skin. Generally, at least a portion of the topsheet 524 is liquid pervious, permitting liquid to readily penetrate through the thickness of the topsheet 524. One topsheet 24 useful herein is available from BBA Fiberweb, Brentwood, Tenn. as supplier code 055SLPV09U. The topsheet 524 may be apertured.

Any portion of the topsheet 524 may be coated with a lotion or skin care composition as is known in the art. Non-limiting examples of suitable lotions include those described in U.S. Pat. Nos. 5,607,760; 5,609,587; 5,635,191; and 5,643,588. The specific examples are not limiting, as any lotion or skin care composition known in the art may be utilized. The topsheet 524 may be fully or partially elasticized or may be foreshortened so as to provide a void space between the topsheet 524 and the core 528. Exemplary structures including elasticized or foreshortened topsheets are described in more detail in U.S. Pat. Nos. 4,892,536; 4,990,147; 5,037,416; and 5,269,775.

Absorbent Core:

The absorbent core 528 may comprise a wide variety of liquid-absorbent materials commonly used in disposable diapers and other absorbent articles. Examples of suitable absorbent materials include comminuted wood pulp, which is generally referred to as air felt creped cellulose wadding; melt blown polymers, including co-form; chemically stiffened, modified or cross-linked cellulosic fibers; tissue, including tissue wraps and tissue laminates; absorbent foams; absorbent sponges; superabsorbent polymers; absorbent gelling materials; or any other known absorbent material or combinations of materials. In one embodiment, at least a portion of the absorbent core is substantially cellulose free and contains less than 10% by weight cellulosic fibers, less than 5% cellulosic fibers, less than 1% cellulosic fibers, no more than an immaterial amount of cellulosic fibers or no cellulosic fibers. It should be understood that an immaterial amount of cellulosic material does not materially affect at least one of the thinness, flexibility, and absorbency of the portion of the absorbent core that is substantially cellulose free. Among other benefits, it is believed that when at least a portion of the absorbent core is substantially cellulose free, this portion of the absorbent core is significantly thinner and more flexible than a similar absorbent core that includes more than 10% by weight of cellulosic fibers. The amount of absorbent material, such as absorbent particulate polymer material present in the absorbent core may vary, but in certain embodiments, is present in the absorbent core in an amount greater than about 80% by weight of the absorbent core, or greater than about 85% by weight of the absorbent core, or greater than about 90% by weight of the absorbent core, or greater than about 95% by weight of the core. The absorbent material 528 may be at least partially surrounded by a core wrap.

In some embodiments, the core may comprise one or more channels 529, which are substantially free of absorbent material. In one nonlimiting example, one or more channels may extend longitudinally.

Nonlimiting exemplary absorbent structures for use as the absorbent core 528 are described in U.S. Pat. Nos. 4,610,678; 5,260,345; 5,387,207; 5,397,316; 5,625,222, 8,979,815, 9,060,904, and 9,072,634; and U.S. patent application Ser. No. 13/491,642.

As disclosed above, in some embodiments, a laminate 10 is not attached to the absorbent core 528. In this way, the materials of the absorbent core 528 do not counteract or otherwise interfere with the ability of the laminate 10 to stretch.

Backsheet:

The backsheet 526 is generally positioned such that it may be at least a portion of the garment-facing surface 504 of the absorbent article 500. Backsheet 526 may be designed to prevent the exudates absorbed by and contained within the absorbent article 20 from soiling articles that may contact the absorbent article 20, such as bed sheets and undergarments. The backsheet 526 is impervious to liquids. Suitable backsheet 526 materials include films such as those manufactured by Tredegar Industries Inc. of Terre Haute, Ind. and sold under the trade names X15306, X10962, and X10964. Other suitable backsheet 26 materials may include breathable materials that permit vapors to escape from the absorbent article 500 while still preventing exudates from passing through the backsheet 526. Exemplary breathable materials may include materials such as woven webs, nonwoven webs, polymeric films such as thermoplastic films of polyethylene or polypropylene, composite materials such as film-coated nonwoven webs, and microporous films such as manufactured by Mitsui Toatsu Co., of Japan under the designation ESPOIR NO and by EXXON Chemical Co., of Bay City, Tex., under the designation EXXAIRE. Suitable breathable composite materials comprising polymer blends are available from Clopay Corporation, Cincinnati, Ohio under the name HYTREL blend P18-3097. Such breathable composite materials are described in greater detail in PCT Application No. WO 95/16746 and U.S. Pat. No. 5,865,823. Other breathable backsheets including nonwoven webs and apertured formed films are described in U.S. Pat. No. 5,571,096. An exemplary, suitable backsheet is disclosed in U.S. Pat. No. 6,107,537. Other suitable materials and/or manufacturing techniques may be used to provide a suitable backsheet 526 including, but not limited to, surface treatments, particular film selections and processing, particular filament selections and processing, etc. In one nonlimiting example, the backsheet is a thermoplastic film having a thickness of from about 0.012 mm to about 0.051 mm.

Backsheet 526 may also consist of more than one layer. The backsheet 526 may comprise an outer cover 526a and an inner layer 526b. The outer cover may be made of a soft, non-woven material. The inner layer may be made of a substantially liquid-impermeable film, such as a polymeric film. The outer cover and an inner layer may be joined together by adhesive or any other suitable material or method. A particularly suitable outer cover is available from Corovin GmbH, Peine, Germany as supplier code A18AH0, and a particularly suitable inner layer is available from RKW Gronau GmbH, Gronau, Germany as supplier code PGBR4WPR.

Figure 21A:
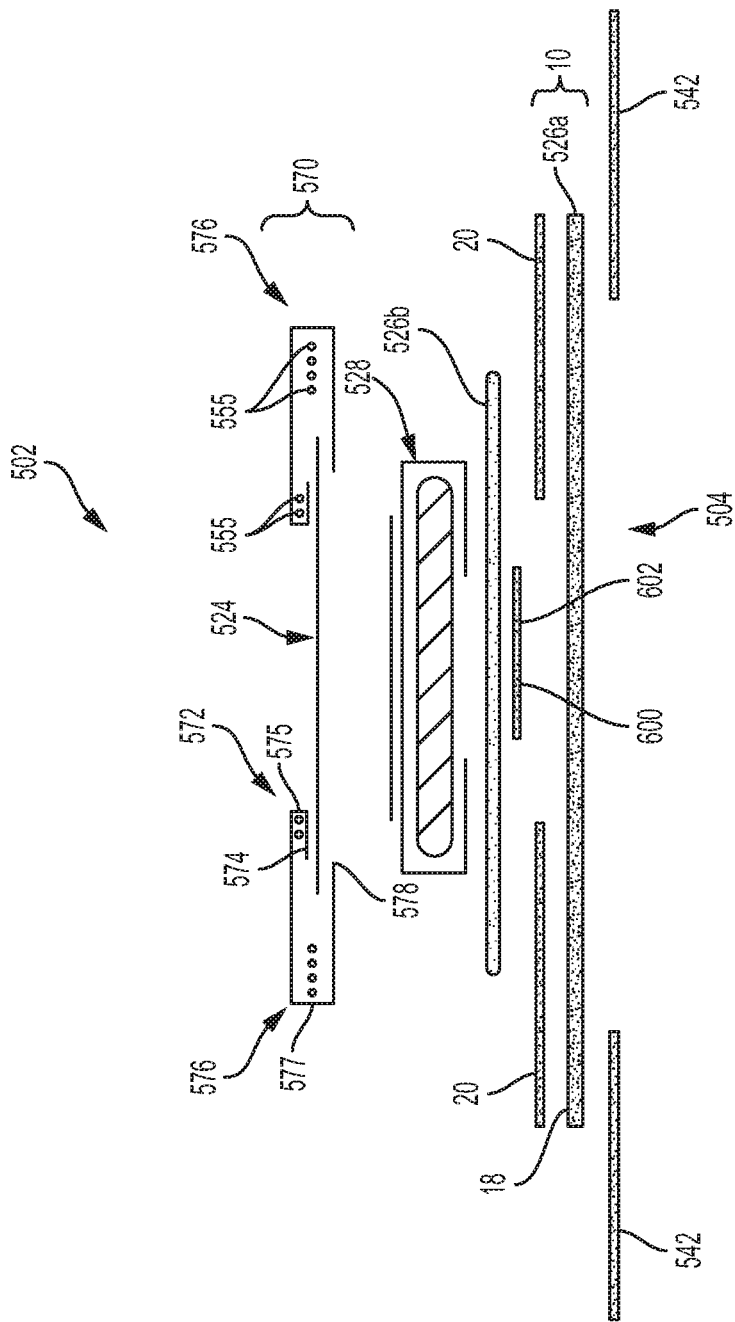
FIGS. 21a-21b are a schematic cross-sectional view of an exemplary embodiments of the leg gasketing systems and topsheet of FIG. 20, the cross section taken along line 21-21. The leg gasketing systems are shown in a flat, uncontracted state.

Turning to FIG. 21a, the backsheet may comprise one or more laminates 10 of the present invention. In some embodiments, the outer cover 526a forms a layer of the laminate 10. In one nonlimiting example, the outer cover 526a or portion(s) of the outer cover are pre-SELFed, such that the outer cover (or said portions of the outer cover) comprises the pre-SELFed layer 18. An elastomeric layer 20 is then joined to the pre-SELFed layer to form the laminate. The elastomeric layer 20 may be any of the type discussed above, including but not limited to an elastomeric laminate layer 224.

Figure 21B:
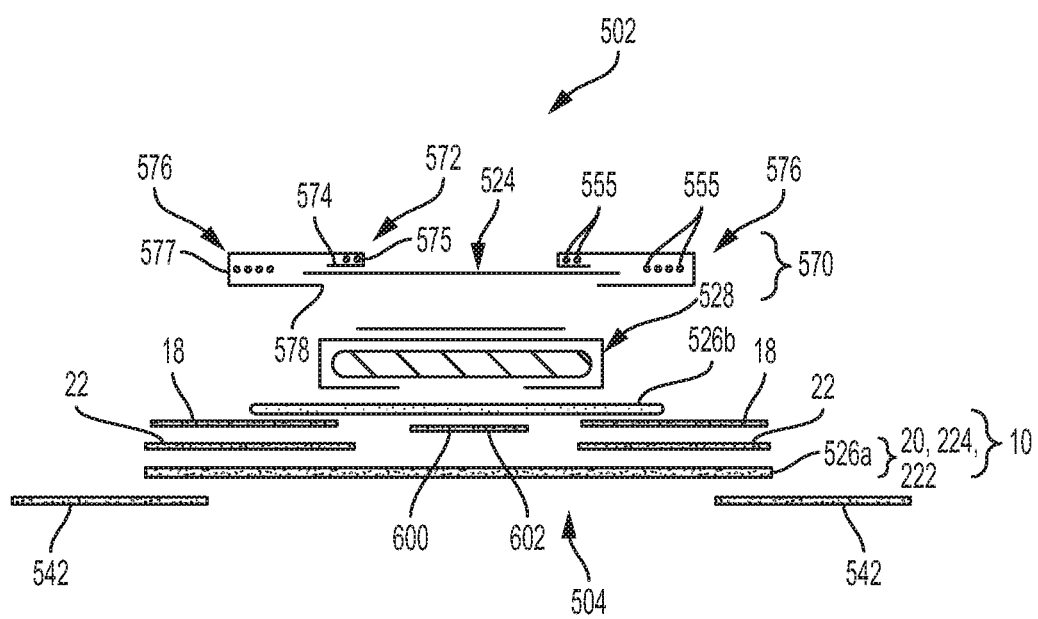

Alternatively, as shown in FIG. 21b, the outer cover 526a may be joined to one or more elastomeric materials 22 and the resulting combination can be activated, forming an elastomeric laminate layer 224 which is an activated elastomeric material 222. One or more pre-SELFed coverstock layer(s) 18 may then be joined to elastomeric laminate layer 224, forming the laminate(s) 10.

Any configuration of the laminate 10 described herein may be incorporated into the backsheet to the extent workable. By incorporating laminates 10, the backsheet 526 becomes stretchable without the need to activate through the total thickness of the backsheet.

As explained above, one or more edges of the laminate may be left non-elastomeric in order to more effectively secure said edge to additional components of the article. Alternatively, the entire laminate 10 in the backsheet may be elastomeric.

The laminate 10 may extend the maximum lateral and/or longitudinal dimensions of the backsheet. Alternatively, the laminate 10 may extend for a portion of the longitudinal dimension of the article. The laminate 10 may be present in one or more of the first waist region, second waist region or crotch region. In a further embodiment, the laminate 10 may extend for a portion, but not the entire width of the backsheet. In still further embodiments, a laminate 20 may comprises edges that are at least partially coterminous with lateral edges of the backsheet and/or edges that are at least partially coterminous with the longitudinal edges of the backsheet.

In some embodiments, as shown in FIGS. 21a-21b, two or more separate laminates 10 are incorporated into the backsheet.

Although FIGS. 21a-21b depict an elastomeric layer 20 positioned above the outer cover 526a, an elastomeric material 22 or elastomeric layer 20 could be positioned below the outer cover 526a (i.e., on the garment-facing side 504 of the article). The laminate 10 may be incorporated into the backsheet in any workable fashion. Having the outer cover 526a be a portion of the laminate 10 provides for stretchability while maximizing the impermeability features of the outer cover. Further, the arrangement of the laminate in FIGS. 21a-21b (where the elastomeric layer is on the body facing side of the outer cover) may also provide a more desirable outer appearance, without any loose edges of the laminate 10 being visible.

Figure 22A:
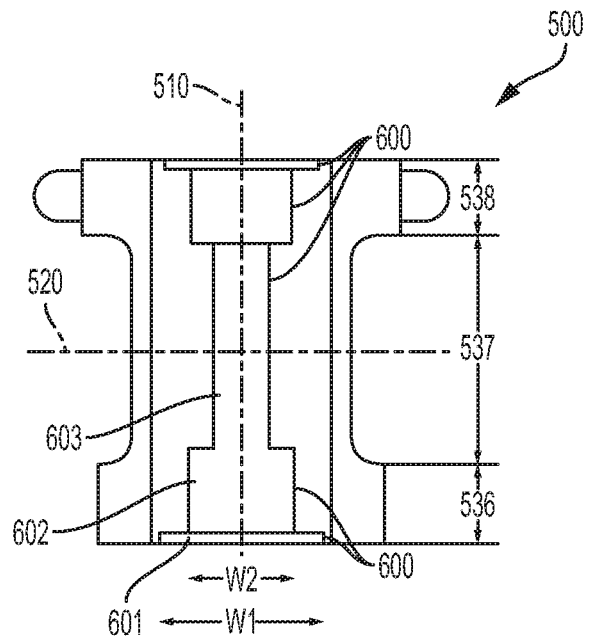
FIGS. 22a-22b are schematic plan views of portions of exemplary absorbent articles including exemplary attachment areas in accordance with nonlimiting embodiments of the present invention.
Figure 22B:
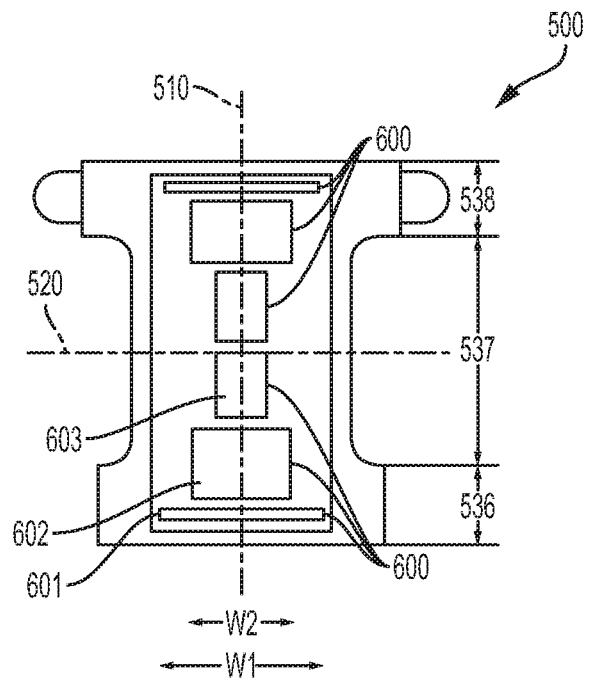

Because bonding may inhibit stretchability, the outer cover 526a may be partially unattached from the inner layer 526b such that the outer cover can extend independent of the inner layer 526b and/or independent of the remaining article layers. The outer cover 526a may be joined to the inner layer 526b by two or more attachment areas 600 having different dimensions. As can be seen in FIGS. 22a-b, a first attachment area 601 may comprises a first width, W1, and may be disposed at or proximate to a waist edge. The first width, W1, may extend for the majority of the width of the article; for example, the first width may extend the majority of width of the inner layer 526b, the majority of the width of the absorbent core, the majority of the width of the topsheet and/or to a cuff edge 577. A second attachment area 602 may be disposed longitudinally inboard of the first attachment area 601 and may comprise a second width, W2. The second width, W2, may be less than the first width, W1. The narrower second attachment area minimizes the dampening effect that bonding has on the degree of extensibility of components of the article (e.g., the laminate 10, leg cuffs 570, etc.).

In some embodiments, an attachment area 600 joins a laminate 10 to the inner layer 526b and/or to another layer of the article. In one nonlimiting example, the attachment area 600 overlaps or coincides with one or more edges of a laminate 10. In a further nonlimiting example, the second attachment area 602 joins the laminate to the inner layer 526b and/or to another layer. The backsheet may comprise further attachment areas, including a third attachment area 603 that is narrower than the first and/or second attachment areas. Exemplary bonding methods for partially attaching the outer cover to the inner layer can be found in U.S. Pat. Nos. 8,569,571, 8,124,828, and 5,575,783.

While a variety of backsheet configurations are contemplated herein, it would be obvious to those skilled in the art that various other changes and modifications can be made without departing from the spirit and scope of the invention.

Ears/Fasteners:

The absorbent article 500 may include front ears 540 and/or back ears 542 as shown in FIG. 20. The ears may be an integral part of the chassis, such as formed from the topsheet 524 and/or backsheet 526 as side panels. Alternatively, the ears may be separate elements attached by gluing, heat embossing, and/or pressure bonding. Each ear may be extensible or inextensible. The ears 540, 542 may be formed from nonwoven webs, woven webs, knitted fabrics, polymeric and elastomeric films, apertured films, sponges, foams, scrims, and combinations and laminates thereof. In some embodiments, the ear may include elastomers (e.g., elastic strands, LYCRA® fibers), such that the ear is stretchable. In certain embodiments, the ears may be formed of a stretch laminate. One or more of the ears 540, 542 may comprise the laminate 10 of the present disclosure.

The absorbent article 500 may also include a fastening system 544. When fastened, the fastening system 544 interconnects the first waist region 536 and the rear waist region 538 resulting in a waist circumference that may encircle the wearer during wear of the absorbent article 20. The fastening system 544 may comprise a fastener 546 such as tape tabs, hook and loop fastening components, interlocking fasteners such as tabs & slots, buckles, buttons, snaps, and/or hermaphroditic fastening components, although any other known fastening means are generally acceptable. Some exemplary surface fastening systems are disclosed in U.S. Pat. Nos. 3,848,594; 4,662,875; 4,846,815; 4,894,060; 4,946,527; 5,151,092; and 5,221,274. An exemplary interlocking fastening system is disclosed in U.S. Pat. No. 6,432,098. The fastening system 544 may also provide a means for holding the article in a disposal configuration as disclosed in U.S. Pat. No. 4,963,140. The fastening system 544 may also include primary and secondary fastening systems, as disclosed in U.S. Pat. No. 4,699,622. The fastening system 544 may be constructed to reduce shifting of overlapped portions or to improve fit as disclosed in U.S. Pat. Nos. 5,242,436; 5,499,978; 5,507,736; and 5,591,152.

In some embodiments, the fastening system 544 and/or the fastener 546 is foldable. In further embodiments, the fastening system comprises the elastomeric laminate 10 in accordance with the present disclosure.

Stretchable ears and/or fastening members may facilitate the attachment of the fastening members to a landing zone and/or maintain the taped diapers in place around the wearer's waist. Further, extensible ears and/or fastening members may provide a more comfortable and contouring fit by initially conformably fitting the absorbent article to the wearer and sustaining this fit throughout the time of wear well past when absorbent article has been loaded with fluids or other bodily exudates since the elasticized ears allow the sides of the absorbent article to expand and contract.

Exemplary ears and/or fastening systems are disclosed in U.S. Pat. Nos. 6,863,666; 6,132,411; 7,870,652; 8,992,499; 8,690,852; 8,382,736.

Leg Gasketing System

Turning to FIG. 21a, the absorbent article 500 may comprise a leg gasketing system 570 attached to the chassis 22, which may comprise one or more cuffs 571. The gasketing system may further comprise the elastomeric laminate 10 in order provide extensibility and one or more of the afore-described benefits to a cuff 571.

The leg gasketing system may comprise a pair of barrier leg cuffs 572. Each barrier leg cuff may be formed by a piece of material which is bonded to the absorbent article so it may extend upwards from a wearer-facing surface of the absorbent article and provide improved containment of fluids and other body exudates approximately at the junction of the torso and legs of the wearer. The barrier leg cuffs are delimited by a proximal edge 574 joined directly or indirectly to the topsheet 524 and/or the backsheet 526 and a free terminal edge 575, which is intended to contact and form a seal with the wearer's skin. In some embodiments, the free terminal edge 575 comprises a folded edge as shown in FIGS. 21a-21b. The barrier leg cuffs 572 extend at least partially between the front waist edge 513 and the rear waist edge 514 of the absorbent article on opposite sides of the longitudinal axis 510 and are at least present in the crotch region. The barrier leg cuffs may be joined at the proximal edge 574 with the chassis of the article by a bond which may be made by gluing, fusion bonding, or a combination of other suitable bonding processes.

The barrier leg cuffs may be integral with the topsheet 524 or the backsheet 526 or may be a separate material joined to the article's chassis. Each barrier leg cuff 572 may comprise one, two or more elastic elements 555 close to the free terminal edge 575 to provide a better seal. Additionally or alternatively, one or both of the barrier cuffs 572 may comprise the elastomeric laminate 10.

In addition to the barrier leg cuffs 572, the article may comprise gasketing cuffs 576, which are joined to the chassis of the absorbent article, in particular to the topsheet 524 and/or the backsheet 526 and are placed externally relative to the barrier leg cuffs 572. The gasketing cuffs 576 may provide a better seal around the thighs of the wearer. A gasketing cuff may comprise a proximal edge 578 and a free terminal edge 577. The free terminal edge 577 may comprise a folded edge. Each gasketing cuff may comprise one or more elastic elements 555 in the chassis of the absorbent article between the topsheet 524 and backsheet 526 in the area of the leg openings. Additionally or alternatively, one or both of the gasketing cuffs 576 may comprise the elastomeric laminate 10. All, or a portion of, the barrier leg cuffs and/or gasketing cuffs may be treated with a lotion or another skin care composition.

In further embodiments, the leg gasketing system comprises barrier leg cuffs that are integral with gasketing cuffs as depicted in FIGS. 21a-21b.

Suitable leg gasketing systems which may be part of the absorbent article and/or modified to include the laminate of the present invention are disclosed in U.S. Pat. App. No. 62/134,622, Ser. No. 14/077,708; U.S. Pat. Nos. 8,939,957; 3,860,003; 7,435,243; 8,062,279.

Elastic Waist Feature

The absorbent article 500 may comprise at least one elastic waist feature 581 that helps to provide improved fit and containment, as shown in FIG. 20. The elastic waist feature 581 is generally intended to expand and contract to dynamically fit the wearer's waist. In some embodiments, the laminate 10 can be used to provide extensibility and/or other benefits to the waist feature 581. Elasticized waist features include waistbands, waist cuffs having pockets formed from a portion of the waist feature 581 that is unattached from the chassis 522, and waist panels designed to fit securely about the abdomen of the wearer. Nonlimiting examples of elasticized waist features are disclosed in U.S. patent application Ser. Nos. 13/490,543; 14/533,472; and 62/134,622. Waist features 581 may be joined to the chassis 522 in the first waist region 536 and/or in the second waist region 538.

Figure 23A:
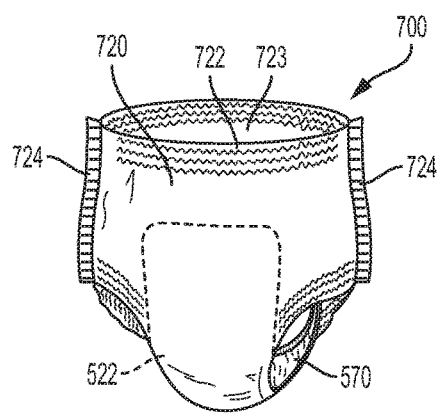
FIG. 23a is a perspective view of an exemplary absorbent pant according to one nonlimiting embodiment of the present invention.
Figure 23B:
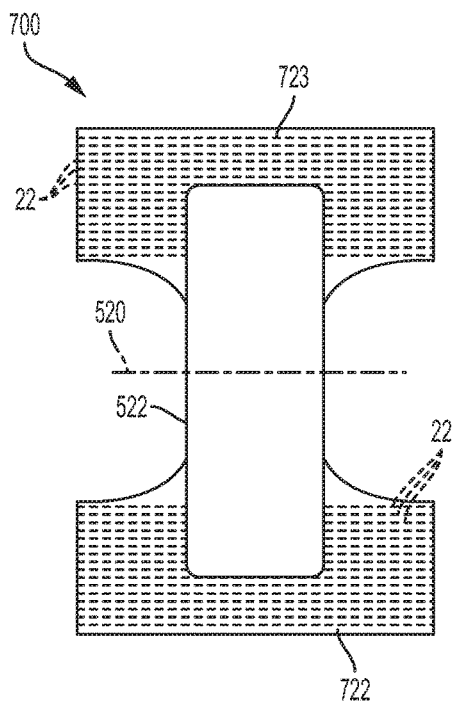
FIG. 23b is a schematic plan view of an exemplary absorbent pant precursor structure, prior to joining of the front and rear sections of the belt.

In some embodiments, the article 500 may comprise an absorbent pant 700 as shown in FIGS. 23a-23b. The absorbent pant may comprise include a chassis 522, a belt 720 to be positioned about the wearer's waist, and optionally a leg gasketing system 570. FIG. 23b depicts an exemplary precursor structure of the pant in FIG. 23a, in an open configuration laid out flat and stretched out laterally against elastic-induced contraction. In the final assembly of the pant, the front belt portion 722 is joined to rear belt portion 723 at seams 724. The belt 720 may be elastomeric. Exemplary belt and absorbent pant constructions are disclosed in U.S. patent application Ser. Nos. 14/598,783 and 14/032,595. The belt may also include one or more fasteners. When fasteners are prefastened in the package, the product becomes a refastenable pant. If the fasteners are not prefastened, the product is a traditional taped diaper which includes a belt.

In some embodiments, the belt 720 may comprise one or more laminates 10 of the present invention. In one nonlimiting example, one or both of the front and rear belt portions comprise layers of coverstock material 17 with an elastomeric material 22 sandwiched between the coverstock layers. One or both of the coverstock layers may be pre-SELFed. Any workable configuration of a laminate 10 as disclosed herein may be incorporated into the belt 720, or into the absorbent pant 700.

Hip Panels

The article 500 may further comprise a stretchable hip panel 596 positioned in the second waist region 538 and/or in the crotch region 537 as shown in FIG. 20. Hip panels add stretch to the middle back of the article, permitting expansion of the back waist region and thereby creating a better fit about the hips and the buttocks of the wearer. An exemplary hip panel is disclosed in U.S. Pat. No. 5,575,783. The elastomeric laminate 10 of the present invention may be used in a hip panel to provide the desired extensibility and the afore-described benefits. In some embodiments, hip panels are formed by incorporating one or more laminates into the backsheet as described in detail above.

Combinations

A. A method for forming an elastomeric laminate (10) that is extensible in a first extensibility direction (FE) comprising the steps of:

providing a first coverstock material (17);
activating the first coverstock material by passing the first coverstock material under tension between the surfaces of a pair of stretching members having discontinuously intermeshing ridges and valleys, and thereby forming a pre-activated layer (18) having a primary activation pattern (28) comprising land areas (242) that extend in the first extensibility direction;
providing an elastomeric layer (20); and
joining the elastomeric layer to the pre-activated layer at one or more bonding sites (400).

B. The method of paragraph A wherein the elastomeric layer is joined to the pre-activated layer at zero relative strain.

C. The method of paragraph A further comprising the steps:
elongating one of the elastomeric layer and the pre-activated layer to form a strained layer such that strained layer comprises a greater strain than the other of elastomeric layer and the pre-activated layer; and
joining the elastomeric layer to the pre-activated layer, such that the elastomeric layer and pre-activated coverstock layer form a gathered laminate.

D. The method of paragraph C wherein the strained layer comprises the elastomeric layer.

E. The method of paragraph C wherein the strained layer comprises the pre-activated layer.

F. The method of any of paragraphs C-E wherein the elastomeric layer and/or the pre-activated layer comprises a zero strain laminate.

G. The method of any of the paragraphs A-E further comprising the steps of providing a second coverstock material; activating the second coverstock material to create a second pre-activated coverstock layer having a secondary activation pattern; and joining the second pre-activated coverstock layer to the elastomeric layer and/or to the pre-activated coverstock layer.

H. The method of paragraph G wherein activating the second coverstock comprises ringrolling the second coverstock material.

I. The method of paragraph G wherein activating the second coverstock material is further characterized by passing the second coverstock material under tension between the surfaces of a pair of stretching members having discontinuously intermeshing ridges and valleys.

J. The method of any of paragraphs G-I further comprising offsetting the primary and secondary activation patterns.

K. The method of any of paragraphs A-J further comprising step of aligning the one or more bonding sites with the primary activation pattern.

L. The method of any of paragraphs A-K wherein the joining step further comprises uniformly bonding the elastomeric layer to the pre-activated layer.

M. The method of any of paragraphs A-K wherein the joining step further comprises non-uniformly bonding the elastomeric layer to the pre-activated layer.

N. The method of any of paragraphs A-M wherein in the step of activating the first material, the pair of stretching members comprises a uniform pattern.

O. The method of any of paragraphs A-M wherein in the step of activating the first coverstock material, the pair of stretching members comprises a nonuniform pattern.

Test Methods

Samples should be sufficient to provide for a gauge length of at least 15 mm along the direction of stretch in the Test, and should be of a constant width (perpendicular to the direction of stretch in the Test) of at least 5 mm. If the sample to be tested is joined to an article, cut if from the article. If testing a laminate, ensure that each layer of the laminate are present in the sample. If testing a layer of the laminate (e.g., elastomeric layer), remove the remaining layers of the laminate prior to testing the sample. Note, as discussed herein, the laminate may be included in various components of an article. As such, the direction of stretch may vary based on the location of the sample in the article. For example, the direction of stretch of leg cuffs is in the longitudinal direction of the article while the direction of stretch in a waist feature is in the lateral direction of the article. If the sample is elastomeric or extensible in either the longitudinal or the lateral directions or both directions, it is within the scope of the present invention.

The Hysteresis Test can be used to various specified strain values. The Hysteresis Test utilizes a commercial tensile tester (e.g., from Instron Engineering Corp. (Canton, Mass.), SINTECH-MTS Systems Corporation (Eden Prairie, Minn.) or equivalent) interfaced with a computer. The computer is used to control the test speed and other test parameters and for collecting, calculating, and reporting the data. The tests are performed under laboratory conditions of 23° C.±2° C. and relative humidity of 50%±2%. The samples are conditioned for 24 hours prior to testing.

Test Protocol

1. Select the appropriate grips and load cell. The grips must have flat surfaces and must be wide enough to grasp the sample along its full width. Also, the grips should provide adequate force to ensure that the sample does not slip during testing. The load cell is selected so that the tensile response from the sample tested is between 25% and 75% of the capacity of the load cell used.

2. Calibrate the tester according to the manufacturer's instructions.

3. Set the distance between the grips (gauge length) at 15 mm.

4. Place the sample in the flat surfaces of the grips such that the uniform width lies along a direction perpendicular to the gauge length direction. Secure the sample in the upper grips, let the sample hang slack, then close the lower grips. Set the slack preload at 0.02 N/cm. This means that the data collection starts when the slack is removed (at a constant crosshead speed of 10 mm/min) with a force of 0.02 N/cm. Strain is calculated based on the adjusted gauge length ($l_{ini}$), which is the length of the sample in between the grips of the tensile tester at a force of 0.02 N/cm. This adjusted gauge length is taken as the initial sample length, and it corresponds to a strain of 0%. Percent strain at any point in the test is defined as the change in length divided by the adjusted gauge length times 100.

5(a) First cycle loading: Pull the sample to the specified strain (herein, 25%) at a constant cross head speed of 100 mm/min. Report the stretched sample length between the grips as $l_{max}$.

5(b) First cycle unloading: Hold the sample at the specified strain for 30 seconds and then return the crosshead to its starting position (0% strain or initial sample length, $l_{ini}$) at a constant cross head speed of 100 mm/min. Hold the sample in the unstrained state for 1 minute.

5(c) Second cycle loading: Pull the sample to the specified strain at a constant cross head speed of 100 mm/min.

5(d) Second cycle unload: Next, return the crosshead to its starting position (i.e. 0% strain) at a constant cross head speed of 100 mm/min.

A computer data system records the force exerted on the sample during the test as a function of applied strain. From the resulting data generated, the following quantities are reported (note that loads are reported as force divided by the width of the sample and do not take into account the thickness of the sample):

i. Length of sample between the grips at a slack preload of 0.02 N/cm ($l_{ini}$) to the nearest 0.001 mm.

ii. Length of sample between the grips on first cycle at the specified strain ($l_{max}$) to the nearest 0.001 mm.

iii. Length of sample between the grips at a second cycle load force of 0.02 N/cm ($l_{ext}$) to the nearest 0.001 mm.

iv. % set, which is defined as $(l_{ext}-l_{ini})/(l_{max}-l_{ini})*100\%$ to the nearest 0.01%.

The testing is repeated for six separate samples and the average and standard deviation reported.

The Hysteresis Test can be suitably modified depending on the expected attributes and/or properties of the particular material sample to be measured. For example, where a sample of the length and width specified above are not available from the subject article, the crosshead speed is adjusted to maintain the same strain rate as that which would be achieved using a 15 mm gauge length and 100 mm/min crosshead speed. As another example, the specified strain may be changed to determine elasticity at different strain levels. In some embodiments, the specified strain is about 50% or more, or about 100% or more, or from about 25% to about 200%, reciting for each range every 10% increment therein.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for forming an elastomeric laminate comprising the steps of:

providing a first coverstock material;

SELF'ing the first coverstock material to create a pre-SELFed coverstock layer having a primary activation pattern comprising SELF-specific land areas and deformed areas;

providing an elastomeric layer; and joining the elastomeric layer at zero strain to the pre-SELFed layer in a relaxed state wherein the deformed areas exist, such that the elastomeric layer and pre-SELFed coverstock layer are joined at one or more bonding sites.

2. The method of claim 1 further comprising the steps of providing a second coverstock material; activating the second coverstock material to create a second pre-activated coverstock layer having a secondary activation pattern; and joining the second pre-activated coverstock layer to the elastomeric layer and/or to the pre-SELFed coverstock layer.

3. The method of claim 2 wherein activating the second coverstock material further comprises SELF'ing the second coverstock material.

4. The method of claim 2 further comprising offsetting the primary and secondary activation patterns.

5. The method of claim 1 wherein the joining step is achieved by one of adhesive, thermal bonding, and/or mechanical bonding.

6. The method of claim 1 wherein the joining step further comprises uniformly bonding the elastomeric layer to the pre-SELFed coverstock layer.

7. The method of claim 1 further comprising the step of aligning the one or more bonding sites with the primary activation pattern.

8. The method of claim 1 wherein the joining step further comprises non-uniformly bonding the elastomeric layer to the pre-SELFed coverstock material.

9. The method of claim 1 wherein the SELF'ing step further comprises SELF'ing the first coverstock material with a uniform SELF pattern.

10. The method of claim 1 wherein the SELF'ing step further comprises SELF'ing the first coverstock material with a nonuniform SELF pattern.

11. A method for forming an elastomeric laminate comprising the steps of:

providing a first coverstock material;

SELF'ing the first coverstock material to create a pre-SELFed coverstock layer having a primary activation pattern comprising SELF-specific land areas;

providing an elastomeric layer;

elongating one of the elastomeric layer and the pre-SELFed layer to form a strained layer such that strained layer comprises a greater strain than the other of elastomeric layer and the pre-SELFed layer; and joining the elastomeric layer to the pre-SELFed layer, such that the elastomeric layer and pre-SELFed coverstock layer are joined at one or more bonding sites and form a gathered laminate.

12. The method of claim 11 wherein the strained layer comprises the elastomeric layer.

13. The method of claim 11 wherein the strained layer comprises the pre-SELFed coverstock layer.

14. The method of claim 11 further comprising the steps of providing a second coverstock material; activating the second coverstock material to create a second pre-activated coverstock layer having a secondary activation pattern; and joining the pre-activated second coverstock layer to the elastomeric layer and/or to the pre-SELFed coverstock layer.

15. The method of claim 14 wherein activating the second coverstock material further comprises SELF'ing the second coverstock material.

16. The method of claim 11 wherein the joining step further comprises uniformly bonding the elastomeric layer to the pre-SELFed coverstock layer.

17. The method of claim 11 further comprising the step of aligning the one or more bonding sites with the primary activation pattern.

18. The method of claim 11 wherein the joining step further comprises non-uniformly bonding the elastomeric layer to the pre-SELFed coverstock material.

19. The method of claim 11 wherein the SELF'ing step further comprises SELF'ing the first coverstock material with a uniform SELF pattern.

20. The method of claim 11 wherein the SELF'ing step further comprises SELF'ing the coverstock material with a nonuniform SELF pattern.

* * * * *